(12) United States Patent
Stahmann et al.

(10) Patent No.: US 7,983,759 B2
(45) Date of Patent: Jul. 19, 2011

(54) ADVANCED PATIENT MANAGEMENT FOR REPORTING MULTIPLE HEALTH-RELATED PARAMETERS

(75) Inventors: Jeffrey E. Stahmann, Ramsey, MN (US); John Hatlestad, Burnsville, MN (US); Qingsheng Zhu, Little Canada, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 2251 days.

(21) Appl. No.: 10/323,606

(22) Filed: Dec. 18, 2002

(65) Prior Publication Data

US 2004/0122485 A1 Jun. 24, 2004

(51) Int. Cl.
*A61N 1/37* (2006.01)
(52) U.S. Cl. .......................................................... 607/60
(58) Field of Classification Search ............... 607/59, 607/62, 60, 30
See application file for complete search history.

(56) References Cited

U.S. PATENT DOCUMENTS

| | | | |
|---|---|---|---|
| 4,310,003 A | 1/1982 | Schlager | |
| 4,389,609 A | 6/1983 | Kawamura | |
| 4,494,950 A | 1/1985 | Fischell | |
| 4,519,395 A | 5/1985 | Hrushesky | |
| 4,712,179 A | 12/1987 | Heimer | 364/417 |
| 4,777,960 A | 10/1988 | Berger et al. | |
| 4,796,634 A | 1/1989 | Huntsman et al. | |
| 4,809,697 A | 3/1989 | Causey, III et al. | 128/419 PT |
| 4,825,869 A | 5/1989 | Sasmor et al. | 128/419 PT |
| 4,838,275 A | 6/1989 | Lee | |
| 4,886,064 A | 12/1989 | Strandberg | |
| 4,928,688 A | 5/1990 | Mower | 128/419 |
| 4,967,749 A | 11/1990 | Cohen | |
| 4,987,897 A | 1/1991 | Funke | |
| 5,031,629 A | 7/1991 | DeMarzo | |
| 5,047,930 A | 9/1991 | Martens et al. | |
| 5,097,831 A | 3/1992 | Lekholm | 128/419 D |
| 5,113,869 A | 5/1992 | Nappholz et al. | 128/696 |

(Continued)

FOREIGN PATENT DOCUMENTS

EP 297675 A1 1/1989

(Continued)

OTHER PUBLICATIONS

Lercher, P., "The Impact of the Multicenter Automatic Defibrillator Implantation Trial II in a University Hospital: Do all Patients with Myocardial Infarction and Reduced Left Ventricular Function need an Implantable Cardioverter-Defibrillator?", *Wiener Klinische Wochenschrift*, 1115, Abstract in English,(Mar. 31, 2003),167-174.

(Continued)

*Primary Examiner* — Michael Kahelin
(74) *Attorney, Agent, or Firm* — Schwegman, Lundberg & Woessner, P.A.

(57) ABSTRACT

Systems, devices and methods for reporting multiple health-related parameters are disclosed. One aspect is a programmable device having machine executable instructions for performing a method to report multiple parameters related to a health condition of a patient. In various embodiments, a number of trended health-related parameters, a number of predetermined events corresponding to the number of trended health-related parameters, and a number of alerts associated with the predetermined events are acquired. The number of trended health-related parameters, the number of predetermined events, and the number of alerts are communicated in a manner suitable for use in determining the health condition of the patient. Other aspects and embodiments are provided herein.

38 Claims, 21 Drawing Sheets

U.S. PATENT DOCUMENTS

| | | | |
|---|---|---|---|
| 5,174,289 A | 12/1992 | Cohen | 128/419 |
| 5,226,413 A | 7/1993 | Bennett et al. | 128/419 PG |
| 5,251,626 A | 10/1993 | Nickolls et al. | 607/14 |
| 5,262,944 A * | 11/1993 | Weisner et al. | 600/300 |
| 5,282,838 A | 2/1994 | Hauser et al. | 607/9 |
| 5,292,341 A | 3/1994 | Snell | 607/30 |
| 5,309,919 A | 5/1994 | Snell et al. | |
| 5,311,873 A | 5/1994 | Savard et al. | |
| 5,321,618 A | 6/1994 | Gessman | 364/413.06 |
| 5,372,607 A | 12/1994 | Stone et al. | 607/30 |
| 5,421,830 A | 6/1995 | Epstein et al. | 607/30 |
| 5,431,691 A * | 7/1995 | Snell et al. | 607/27 |
| 5,441,047 A | 8/1995 | David et al. | |
| 5,540,727 A | 7/1996 | Tockman et al. | 607/18 |
| 5,549,654 A | 8/1996 | Powell | 607/32 |
| 5,576,952 A | 11/1996 | Stutman et al. | |
| 5,594,638 A | 1/1997 | Iliff | 395/203 |
| 5,607,460 A | 3/1997 | Kroll et al. | 607/30 |
| 5,613,495 A | 3/1997 | Mills et al. | |
| 5,626,630 A | 5/1997 | Markowitz et al. | |
| 5,630,835 A | 5/1997 | Brownlee | 607/60 |
| 5,666,487 A | 9/1997 | Goodman et al. | |
| 5,690,690 A | 11/1997 | Nappholz et al. | 607/30 |
| 5,693,076 A | 12/1997 | Kaemmerer | |
| 5,697,959 A | 12/1997 | Poore | |
| 5,716,382 A | 2/1998 | Snell | 607/30 |
| 5,720,771 A | 2/1998 | Snell | 607/60 |
| 5,722,999 A | 3/1998 | Snell | 607/32 |
| 5,724,985 A | 3/1998 | Snell et al. | 128/697 |
| 5,752,976 A | 5/1998 | Duffin et al. | |
| 5,759,199 A | 6/1998 | Snell et al. | 607/60 |
| 5,792,064 A | 8/1998 | Panescu et al. | |
| 5,800,473 A | 9/1998 | Faisandier | 607/59 |
| 5,833,623 A | 11/1998 | Mann et al. | 600/523 |
| 5,860,918 A * | 1/1999 | Schradi et al. | 600/300 |
| 5,891,178 A | 4/1999 | Mann et al. | 607/27 |
| 5,911,132 A | 6/1999 | Sloane et al. | |
| 5,935,078 A | 8/1999 | Feierbach | |
| 5,935,081 A | 8/1999 | Kadhiresan | |
| 5,942,986 A | 8/1999 | Shabot et al. | |
| 5,970,986 A | 10/1999 | Bolz et al. | |
| 5,987,519 A | 11/1999 | Peifer et al. | |
| 5,995,939 A | 11/1999 | Berman et al. | |
| 6,001,060 A | 12/1999 | Churchill et al. | |
| 6,015,388 A | 1/2000 | Sackner et al. | |
| 6,016,442 A | 1/2000 | Hsu et al. | 600/518 |
| 6,016,447 A | 1/2000 | Juran et al. | |
| 6,024,089 A | 2/2000 | Wallace et al. | |
| 6,024,699 A | 2/2000 | Surwit et al. | |
| 6,045,513 A | 4/2000 | Stone et al. | |
| 6,070,101 A | 5/2000 | Struble et al. | 607/9 |
| 6,073,048 A | 6/2000 | Kieval et al. | |
| 6,076,015 A | 6/2000 | Hartley et al. | |
| 6,091,990 A | 7/2000 | Hsu et al. | 607/5 |
| 6,093,146 A | 7/2000 | Filangeri | |
| 6,102,874 A | 8/2000 | Stone et al. | |
| 6,112,224 A | 8/2000 | Peifer et al. | |
| 6,115,630 A | 9/2000 | Stadler et al. | |
| 6,168,563 B1 | 1/2001 | Brown | 600/301 |
| 6,190,324 B1 | 2/2001 | Kieval et al. | 600/483 |
| 6,240,317 B1 | 5/2001 | Villaseca et al. | 607/60 |
| 6,249,703 B1 | 6/2001 | Stanton et al. | |
| 6,249,705 B1 | 6/2001 | Snell | |
| 6,250,309 B1 | 6/2001 | Krichen et al. | |
| 6,275,727 B1 | 8/2001 | Hopper et al. | 600/513 |
| 6,280,409 B1 | 8/2001 | Stone et al. | 604/67 |
| 6,304,773 B1 | 10/2001 | Taylor et al. | 600/515 |
| 6,331,160 B1 | 12/2001 | Bardy | |
| 6,336,900 B1 | 1/2002 | Alleckson et al. | |
| 6,336,903 B1 | 1/2002 | Bardy | 600/508 |
| 6,351,675 B1 | 2/2002 | Tholen et al. | 607/59 |
| 6,363,282 B1 | 3/2002 | Nichols et al. | |
| 6,368,284 B1 | 4/2002 | Bardy | 600/508 |
| 6,381,496 B1 | 4/2002 | Meadows et al. | |
| 6,383,136 B1 | 5/2002 | Jordan | 600/300 |
| 6,398,728 B1 | 6/2002 | Bardy | 600/300 |
| 6,411,840 B1 | 6/2002 | Bardy | 600/513 |
| 6,411,847 B1 | 6/2002 | Mower | 607/9 |
| 6,416,471 B1 | 7/2002 | Kumar et al. | |
| 6,434,429 B1 | 8/2002 | Kraus et al. | |
| 6,438,407 B1 * | 8/2002 | Ousdigian et al. | 600/510 |
| 6,438,408 B1 | 8/2002 | Mulligan et al. | |
| 6,440,066 B1 | 8/2002 | Bardy | 600/300 |
| 6,441,747 B1 | 8/2002 | Khair et al. | |
| 6,442,432 B2 | 8/2002 | Lee | |
| 6,442,433 B1 | 8/2002 | Linberg | 607/60 |
| 6,443,890 B1 | 9/2002 | Schulze et al. | |
| 6,453,201 B1 | 9/2002 | Daum et al. | |
| 6,470,215 B1 | 10/2002 | Kraus et al. | |
| 6,480,745 B2 | 11/2002 | Nelson et al. | |
| 6,490,487 B1 | 12/2002 | Kraus et al. | |
| 6,497,655 B1 | 12/2002 | Linberg et al. | |
| 6,514,195 B1 | 2/2003 | Ferek | |
| 6,542,775 B2 | 4/2003 | Ding et al. | |
| 6,544,174 B2 | 4/2003 | West et al. | |
| RE38,119 E | 5/2003 | Mower | 607/9 |
| 6,564,104 B2 | 5/2003 | Nelson et al. | |
| 6,564,105 B2 | 5/2003 | Starkweather et al. | |
| 6,579,231 B1 | 6/2003 | Phipps | |
| 6,585,644 B2 | 7/2003 | Lebel et al. | |
| 6,592,528 B2 | 7/2003 | Amano | |
| 6,622,045 B2 | 9/2003 | Snell et al. | |
| 6,628,989 B1 | 9/2003 | Penner et al. | |
| 6,648,823 B2 | 11/2003 | Thompson et al. | |
| 6,650,939 B2 | 11/2003 | Taepke, II et al. | |
| 6,650,944 B2 | 11/2003 | Goedeke et al. | |
| 6,665,558 B2 | 12/2003 | Kalgren et al. | |
| 6,669,631 B2 | 12/2003 | Norris et al. | |
| 6,684,103 B2 | 1/2004 | Ding et al. | |
| 6,687,547 B2 | 2/2004 | Goedeke et al. | |
| 6,735,479 B2 | 5/2004 | Fabian et al. | |
| 6,738,667 B2 | 5/2004 | Deno et al. | |
| 6,738,671 B2 | 5/2004 | Christophersom et al. | |
| 6,764,446 B2 | 7/2004 | Wolinsky et al. | |
| 6,804,558 B2 | 10/2004 | Haller et al. | |
| 6,811,537 B2 | 11/2004 | Bardy | |
| 6,816,744 B2 | 11/2004 | Garfield et al. | |
| 6,827,670 B1 | 12/2004 | Stark et al. | |
| 6,834,203 B2 | 12/2004 | Bardy | |
| 6,878,112 B2 | 4/2005 | Linberg et al. | |
| 6,931,273 B2 | 8/2005 | Groenewegen et al. | |
| 6,937,899 B2 | 8/2005 | Sheldon et al. | |
| 6,944,495 B2 | 9/2005 | MacAdam et al. | |
| 6,961,617 B1 | 11/2005 | Snell | |
| 6,975,900 B2 | 12/2005 | Rudy et al. | |
| 7,024,248 B2 | 4/2006 | Penner et al. | |
| 7,043,305 B2 | 5/2006 | Kenknight et al. | |
| 7,047,065 B2 | 5/2006 | Kalgren et al. | |
| 7,070,562 B2 | 7/2006 | Bardy | |
| 7,115,096 B2 | 10/2006 | Siejko et al. | |
| 7,123,953 B2 | 10/2006 | Starobin et al. | |
| 7,136,707 B2 | 11/2006 | Hall et al. | |
| 7,203,549 B2 | 4/2007 | Schommer et al. | |
| 7,209,786 B2 | 4/2007 | Brockway et al. | |
| 7,248,923 B2 | 7/2007 | Maile et al. | |
| 7,273,457 B2 | 9/2007 | Penner | |
| 7,275,220 B2 | 9/2007 | Brummel et al. | |
| RE39,897 E | 10/2007 | Mower | |
| 7,431,699 B2 | 10/2008 | Siejko et al. | |
| 7,468,032 B2 | 12/2008 | Stahmann et al. | |
| 7,480,528 B2 | 1/2009 | Brockway et al. | |
| 7,559,901 B2 | 7/2009 | Maile et al. | |
| 7,805,199 B2 | 9/2010 | KenKnight et al. | |
| 2001/0007053 A1 | 7/2001 | Bardy | 600/300 |
| 2001/0012955 A1 | 8/2001 | Goedeke et al. | 607/27 |
| 2001/0031997 A1 | 10/2001 | Lee | |
| 2001/0031998 A1 | 10/2001 | Nelson et al. | |
| 2001/0039375 A1 | 11/2001 | Lee | |
| 2001/0039503 A1 | 11/2001 | Chan et al. | |
| 2001/0047125 A1 * | 11/2001 | Quy | 600/300 |
| 2001/0049471 A1 | 12/2001 | Suzuki et al. | |
| 2001/0049544 A1 | 12/2001 | Lee | |
| 2002/0013613 A1 | 1/2002 | Haller et al. | |
| 2002/0016550 A1 | 2/2002 | Sweeney et al. | 600/515 |
| 2002/0019586 A1 | 2/2002 | Teller et al. | |
| 2002/0023654 A1 | 2/2002 | Webb | |
| 2002/0026103 A1 | 2/2002 | Norris et al. | 600/300 |

| | | | |
|---|---|---|---|
| 2002/0026223 A1 | 2/2002 | Riff et al. ..................... 607/27 | |
| 2002/0045808 A1 | 4/2002 | Ford et al. | |
| 2002/0049482 A1 | 4/2002 | Fabian et al. | |
| 2002/0052539 A1* | 5/2002 | Haller et al. ................ 600/300 | |
| 2002/0077562 A1 | 6/2002 | Kalgren et al. | |
| 2002/0082868 A1 | 6/2002 | Pories et al. | |
| 2002/0103442 A1 | 8/2002 | Mulligan et al. | |
| 2002/0115939 A1 | 8/2002 | Mulligan et al. | |
| 2002/0120311 A1 | 8/2002 | Lindh et al. | |
| 2002/0123672 A1 | 9/2002 | Christophersom et al. ... 600/300 | |
| 2002/0138012 A1 | 9/2002 | Hodges et al. | |
| 2002/0173830 A1 | 11/2002 | Starkweather et al. | |
| 2002/0193667 A1 | 12/2002 | McNair | |
| 2002/0193670 A1 | 12/2002 | Garfield et al. | |
| 2003/0050803 A1 | 3/2003 | Marchosky | |
| 2003/0055406 A1 | 3/2003 | Lebel et al. | |
| 2003/0055679 A1 | 3/2003 | Soll et al. | |
| 2003/0074029 A1 | 4/2003 | Deno et al. | |
| 2003/0088290 A1 | 5/2003 | Spinelli et al. | |
| 2003/0093127 A1 | 5/2003 | Dalal | |
| 2003/0144702 A1 | 7/2003 | Yu et al. | |
| 2003/0144703 A1 | 7/2003 | Yu et al. | |
| 2003/0144711 A1 | 7/2003 | Pless et al. | |
| 2003/0171791 A1 | 9/2003 | KenKnight et al. | |
| 2003/0235816 A1 | 12/2003 | Slawin et al. | |
| 2004/0019287 A1 | 1/2004 | White | |
| 2004/0088192 A1 | 5/2004 | Schmidt et al. | |
| 2004/0117204 A1 | 6/2004 | Mazar et al. | |
| 2004/0122294 A1 | 6/2004 | Hatlestad et al. | |
| 2004/0122295 A1 | 6/2004 | Hatlestad et al. | |
| 2004/0122296 A1 | 6/2004 | Hatlestad et al. | |
| 2004/0122297 A1 | 6/2004 | Stahmann et al. | |
| 2004/0122484 A1 | 6/2004 | Hatlestad et al. | |
| 2004/0122486 A1 | 6/2004 | Stahmann et al. | |
| 2004/0122487 A1 | 6/2004 | Hatlestad et al. | |
| 2004/0133080 A1 | 7/2004 | Mazar | |
| 2004/0230456 A1 | 11/2004 | Lozier et al. | |
| 2005/0021370 A1 | 1/2005 | Riff et al. | |
| 2005/0042589 A1 | 2/2005 | Hatlestad et al. | |
| 2006/0195163 A1 | 8/2006 | KenKnight et al. | |
| 2006/0253300 A1 | 11/2006 | Somberg et al. | |
| 2008/0021287 A1 | 1/2008 | Woellenstein et al. | |
| 2009/0105554 A1 | 4/2009 | Stahmann et al. | |
| 2009/0124917 A1 | 5/2009 | Hatlestad et al. | |
| 2010/0063840 A1 | 3/2010 | Hoyme et al. | |
| 2011/0015701 A1 | 1/2011 | Kenknight et al. | |

FOREIGN PATENT DOCUMENTS

| | | |
|---|---|---|
| EP | 709058 A1 | 5/1996 |
| EP | 10066698 A2 | 1/2001 |
| WO | WO-9914882 A2 | 3/1999 |
| WO | WO-00/41765 | 7/2000 |
| WO | WO-00/41766 | 7/2000 |
| WO | WO-01/03575 | 1/2001 |
| WO | WO-01/24876 A1 | 4/2001 |
| WO | WO-01/67948 A2 | 9/2001 |
| WO | WO-2004/104901 A1 | 12/2004 |

OTHER PUBLICATIONS

Moss, A. J., "MADIT-II: Substudies and Their Implications", *Cardiac Electrophysiology Review*, 7, (Dec. 2003),430-433.

Moss, A. J., "Prophylactic Implantation of a Defibrillator in Patients with Myocardial Infarction and Reduced Ejection Fraction", *The New England Journal of Medicine*, 346, (Mar. 21, 2002),877-883.

Barbaro, V., et al., "A portable unit for remote monitoring of pacemaker patients", *Journal of Telemedicing and Telecare*, vol. 3, No. 2, (1997),96-102.

Bourge, Robert, et al., "Noninvasive Rejection Monitoring of Cardiac Transplants Using High Resolution Intramyocardial Electrograms", *Pace*, vol. 21, Part II (Nov. 1998),2338-2344.

Hutten, H., et al., "Cardiac pacemaker as bridge to cardiac telemonitoring", *Biomedizinische Technik*, 41(6), Institut for Elektro-und Biomedizinische Technik Technische Universitat Graz. English Abstract, (Jun. 1996),158-165.

Hutten, H., et al., "Cardiac Telemonitoring through the Linkage of Close-up Telemetry and Internet Transmission", *Institute for Electro- and Biomedical Technology*, Technical University of Graz Inffeldgasse, 42 English Abstract, (1997),67-69.

Ji, J., "An Ultraminiature CMOS Pressure Sensor for a Multiplexed Cardiovascular Catheter", *IEEE Transactions on Electron Devices*, vol. 39, No. 10, (Oct. 1992),pp. 2260-2267.

Mower, Morton, U.S. Patent Office Patent Application Information Retrieval (PAIR) search results for U.S. Appl. No. 10/214,474, filed Aug. 8, 2002, entitled "*Method and Apparatus for Treating Hemodynamic Disfunction*", 3.

Smith, R.A., et al., "An intranet database for pacemaker patients", *International Journal of Medical Informatics*, 47 (1997),79-82.

Girouard, Steven D., et al., "Cardiac Rhythm Management Systems and Methods Predicting Congestive Heart Failure Status", Application filed Aug. 6, 2002 U.S. Appl. No. 10/213,268, 33 pgs.

Hatlestad, John, "Methods and Devices for Detection of Context When Addressing a Medical Condition of a Patient", Application filed Oct. 11, 2002 U.S. Appl. No. 10/269,611, 29 pages.

Kenknight, Bruce H., et al., "Method and Apparatus for Establishing Context Among Events and Optimizing Implanted Medical Device Performance", filed Mar. 6, 2002 U.S. Appl. No. 10/093,353, 43 pgs.

Zhu, Qingsheng, et al., "Method and Apparatus for Determining Changes in Heart Failure Status", Application filed Nov. 15, 2001 U.S. Appl. No. 10/001,223, 22 pgs.

* cited by examiner

ADVANCED PATIENT MANAGEMENT FOR REPORTING MULTIPLE HEALTH-RELATED PARAMETERS

CROSS REFERENCE TO RELATED APPLICATIONS

This application is related to the following commonly assigned U.S. patent applications which are herein incorporated by reference in their entirety: "Method and Apparatus for Establishing Context Among Events and Optimizing Implanted Medical Device Performance," Ser. No. 10/093,353, filed on Mar. 6, 2002; "Advanced Patient Management For Acquiring, Trending and Displaying Health-Related Parameters," Ser. No. 10/323,859, filed on Dec. 18, 2002; "Advanced Patient Management For Defining, Identifying and Using Predetermined Health-Related Events," Ser. No. 10/323,604, filed on Dec. 18, 2002; "Advanced Patient Management System With Environmental Data," Ser. No. 10/323,590, filed on Dec. 18, 2002; "Advanced Patient Management For Identifying, Displaying And Assisting With Correlating Health-Related Data," Ser. No. 10/323,713, filed on Dec. 18, 2002; "Advanced Patient Management With Composite Parameter Indices," Ser. No. 10/323,860, filed on Dec. 18, 2002; "Advanced Patient Management For Triaging Health-Related Data," Ser. No. 10/323,616, filed on Dec. 18, 2002; and "Advanced Patient Management For Triaging Health-Related Data Using Color Codes," Ser. No. 10/323,607, filed on Dec. 18, 2002.

TECHNICAL FIELD

This application relates generally to medical devices and, more particularly, to reporting multiple parameters in advanced patient management systems.

BACKGROUND

An Implantable Medical Device (IMD) is a medical device designed to be chronically implanted in a human or other organism. Some IMDs include sensors to monitor a patient's condition, and some IMDs have been used to treat a patient. Some examples of IMDs include implantable cardiac rhythm management (CRM) devices such as cardiac pacemakers and implantable cardioverter/defibrillators (ICDs). Other examples of IMDs include a number of monitors or sensors, stimulators and delivery systems for both cardiac-related applications and non-cardiac-related applications.

The sensed data from the IMD is capable of being wirelessly communicated to an external device, and the external device is capable of wirelessly programming the IMD. For example, data from an implantable CRM is capable of being wirelessly communicated to a programmer device. Additionally, the programmer is capable of wirelessly communicating with the implantable CRM to program the CRM to perform a desired device function.

Due to the potentially large amount of data capable of being sensed by one or more IMDs, it is desired to appropriately process the large amount of sensed data to provide meaningful information. The sensed data alone may not be an accurate indication of the overall health of the patient because other factors can significantly influence the sensed data. Thus, it has been proposed to use patient data from other sources. However, this patient data can compound the problem of providing and reporting meaningful data, and still may not provide an accurate indication of the overall health of the patient.

SUMMARY

The above mentioned problems are addressed by the present subject matter and will be understood by reading and studying the following specification. The present subject matter provides for reporting multiple health-related parameters from a variety of sources including data provided by an implanted medical device (IMD) and from other sources.

One aspect is a programmable device having machine executable instructions for performing a method to report multiple parameters related to a health condition of a patient. In various embodiments, a number of trended health-related parameters, a number of predetermined events corresponding to the number of trended health-related parameters, and a number of alerts associated with the predetermined events are acquired. The number of trended health-related parameters, the number of predetermined events, and the number of alerts are communicated in a manner suitable for use in determining the health condition of the patient.

In various embodiments, a number of predetermined events for the health of the patient is defined. A number of health-related parameters is acquired. The number of health-related parameters is trended. At least one of the number of defined predetermined events is detected based on the trended health-related parameters. The at least one detected predetermined event is associated with at least one alert. The trended health-related parameters, the at least one detected predetermined event, and the at least one alert are communicated in a manner suitable for use in determining the health condition of the patient.

One aspect is a device for reporting multiple parameters related to a health condition of a patient. In various embodiments, the device includes a parameter acquisition module, a predetermined event acquisition module, an alert acquisition module, and an output communication module to communicate with the parameter acquisition module, the predetermined event acquisition module, and the alert acquisition module. The parameter acquisition module acquires a number of trended health-related parameters. The predetermined event acquisition module acquires a number of predetermined events corresponding to the number of trended health-related parameters. The alert acquisition module acquires a number of alerts associated with the number of predetermined events. The output communication module communicates the number of trended health-related parameters, the number of predetermined events, and the number of alerts in a manner suitable for use in determining the health condition of the patient.

These and other aspects, embodiments, advantages, and features will become apparent from the following description and the referenced drawings.

DETAILED DESCRIPTION OF THE INVENTION

Figure 1:
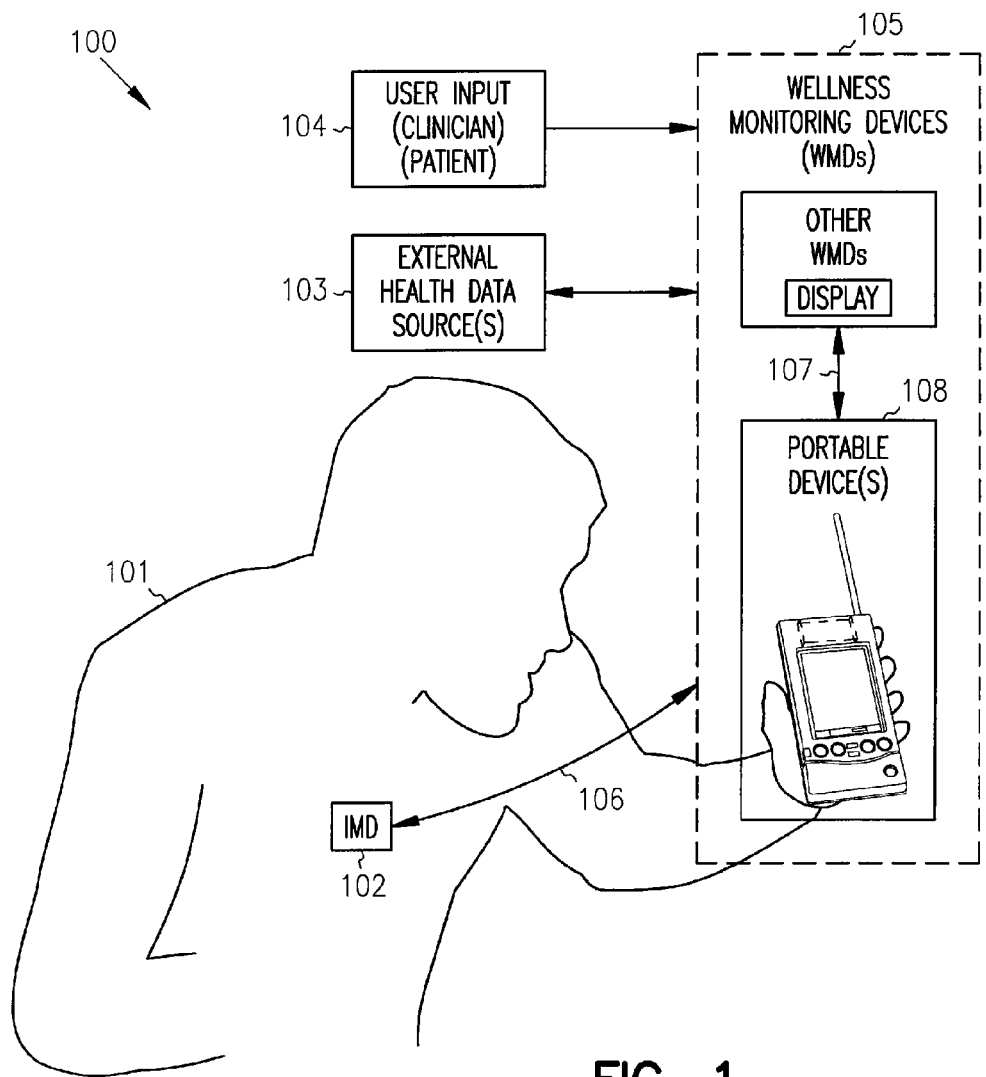
FIG. 1 illustrates an advanced patient management (APM) system according to various embodiments of the present subject matter.

The following detailed description refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. The various embodiments disclosed herein are not necessarily mutually exclusive, as some disclosed embodiments can be combined with one or more other disclosed embodiments to form new embodiments. The following detailed description is, therefore, not to be taken in a limiting sense, and the scope of the present subject matter is defined only by the appended claims, along with the full scope of equivalents to which such claims are entitled.

The present subject matter provides a system to assist with monitoring the overall health of patients, and thus to assess and treat health conditions, by reporting multiple health-related parameters. In various embodiments, a clinician such as a physician monitors the patient's health. In various embodiments, the system includes an implantable medical device (IMD) which is capable of sensing various health-related parameters (also referred to herein as internal health-related parameters) indicative of a health condition. The IMD includes one or more IMD sensors to sense one or more desired internal health-related parameters. In various embodiments, the IMD is capable of providing therapy to treat the health condition. In various embodiments, the system includes an external health data source that includes other health-related parameters (also referred to herein as external health-related parameters). The external health-related parameters can influence the sensed internal health-related parameters. Thus, a combination of internal and external health-related parameters can provide a more accurate view of the patient's health.

In various embodiments, the system includes a user input to collect health-related information that is contributed voluntarily by a user (such as a patient, clinician or other user). This user-volunteered information is an example of external human-resource parameters and is able to be more subjective in nature (compared to the internal health-related parameters determined by sensors or other external health-related parameters such as databases and external sensors), and thus is useful to identify other information that can influence the other health-related parameters. The present subject matter acquires internal and/or external health-related parameters from one or more of these sources, trends the parameters, and displays the trended parameters in a useful manner on a wellness monitoring device to assist with accurately assessing and treating a patient's health condition. As such, the present subject matter is capable of providing a diagnostic context used to interpret the health condition of the patient, and to appropriately adjust the device and/or medical therapy, accordingly.

A large number of health-related parameters are capable of being acquired, trended and displayed according to various embodiments of the present subject matter. For example, a non-exhaustive list of health-related parameters includes heart rate/rhythm including ventricular tachycardia and fibrillation, conduction intervals, ectopic density, atrial fibrillation (AF)/atrial tachycardia (AT) percent, heart rate variability (HRV), activity, lead position, concomitant conditions, temperature, blood pressure, respiration rate/rhythm, pulmonary/peripheral edema, posture, blood gases, stroke volume contractility, filling time, heart sounds, weight, ischemia, cardiac output, after load, medications, device indications, and electromyogram. Other examples of health-related parameters are provided throughout this disclosure.

These health-related parameters are capable of being acquired from a number of data sources. For example, a non-exhaustive list of data sources include IMDs, external device sensors, medication usage monitors, databases, and user inputs by a clinician and/or patient. An IMD, for example, is capable of providing health-related parameters for rhythms, conduction delays, respiration, activity, heart sounds, posture, and the like. External device measurements, for example, are capable of providing health-related parameters for weight, blood pressure, echo pulse oximetry, peripheral edema, and the like. Other examples of IMD health-related parameters and external health-related parameters are provided throughout this disclosure. A physician, for example, is capable of providing health-related parameters for lead positions, indications(s), medications, concomitant conditions, and the like. A medical database, for example, is capable of providing health-related parameters from external device measurements and physician input for medical tests and a large number and a large variety of other parameters. A patient, for example, is capable of providing health-related parameters for diet, medication usage, symptoms, blood pressure, and the like. As technology continues to improve, more and more health-related parameters will be automatically acquired using, for example, an IMD rather than using an external interactive system.

In various embodiments of the present subject matter, the APM system performs various methods related to managing a patient's health. The APM system includes a number of programmable devices with a machine-readable medium having machine-executable instructions. The programmable devices(s) perform the machine-executable instructions to perform the method. In various embodiments, the programmable device includes a processor to perform the machine-executable instructions. In various embodiments, the machine-executable instructions are provided on one or more machine-readable mediums (or media).

FIG. 1 illustrates an advanced patient management system according to various embodiments of the present subject matter. Various embodiments of the system 100 include less than all of the components shown in FIG. 1, and various embodiments of the system 100 include other components than those shown in FIG. 1.

A patient 101 is illustrated with an implantable medical device (IMD) 102. Generally, the IMD includes one or more IMDs that provide internal therapy and/or acquire or sense internal data parameters. In various embodiments, the IMD is a CRM device that provides cardiac rhythm management pulsing and also senses one or more physiological parameters of a heart. Other IMDs that sense parameters and/or provide therapy, including various electrical and drug therapy, are within the scope of the present subject matter.

In various embodiments, at least one IMD 102 provides internal data such as heart rhythm, breathing, and activity. Other types of data derived from IMDs are also contemplated. For example, in one embodiment, a respiration sensor is implanted into patient and communicates with portable device. Data received from such IMDs may be perceived as involuntary, or passive, data since the patient has no control over the process of collecting and transmitting the data from such sources. In various embodiments, IMD-provided data includes parameters sensed by the IMD and/or parameters provided by interrogating the IMD to obtain device performance status.

The illustrated system also includes one or more external data source(s) 103 that provide health-related parameters. The external health-related parameters supplement the internal parameters and/or provide a diagnostic context to the internal health-related parameters. Examples of external source(s) of health data include: external sensing devices such as body temperature thermometers, blood pressure monitors, and the like; room temperature thermometers, light sensors and the like; databases such as patient history databases that are found hospitals or clinics and that may include information such as medical test results and family history; a web server database (a database accessible through a global communication network—e.g. Internet) that may include information regarding environment, medication interaction, and the like; databases and/or user inputs regarding mental/emotional and diet parameter types; and other external data sources capable of providing health-related parameters. One definition of the term mental is something that is of or relates to the mind. One definition of the term emotional is a strong feeling, aroused mental state, or intense state of drive or unrest, which may be directed toward a definite object and is evidenced in both behavior and in psychologic changes, with accompanying autonomic nervous system manifestations.

The illustrated system also includes a user input 104 through which a user is able to input additional health-related parameters for use by a wellness monitoring device (WMD) 105. In various embodiments, the user input 104 includes a touch screen on a PDA or other device, a keyboard and mouse on a computer, and the like. In various embodiments, a patient is able to input additional health-related parameters for use by the wellness monitoring device. In various embodiments, a clinician is able to input additional health-related parameters for use by the WMD.

The WMD 105 is illustrated by dotted line, and includes one or more devices. In various embodiments, the at least one IMD 102 communicates wirelessly with at least one WMD 105, as shown by communication link 106. In various embodiments that include multiple WMDs, the WMDs are able to communicate with each other, as shown via communication link 107. In various embodiments, the WMD(s) includes portable devices 108 that are external to the body of patient such as a PDA, (variously referred to as a personal digital, or data, assistant), a portable telephone (including a cellular telephone or a cordless telephone), a pager (one way or two way), a handheld, palm-top, laptop, portable or notebook computer, or other such battery operated portable communication device. In various embodiments, the WMD(s) includes programmers. In various embodiments, the WMD(s) includes various non-portable devices such as larger computers or computer enterprise systems.

In various embodiments of the present subject matter, the WMD 105 (which includes one or more devices) includes a display on which parameter trends are capable of being displayed. In various embodiments, the portable device 108 includes a touch-sensitive display screen for displaying information to a user or patient. Depending on the application executing on the portable device 108, the display screen may provide prompts, messages, questions, or other data designed to elicit an input from patient. Examples of such prompts are provided in the patent application entitled "Method and Apparatus for Establishing Context Among Events and Optimizing Implanted Medical Device Performance," Ser. No. 10/093,353, filed on Mar. 6, 2002, which has previously been incorporated by reference in its entirety. Data received from such interactive prompts may be perceived as voluntary, or active, data since the cooperation and active input of the patient is part of the data collection process. In various embodiments, the user input data may be received from a user based on a prompt provided to the user, on an ad hoc basis as determined by the user, or as determined by a processor. The user may enter data using a menu based system, a graphical user interface (GUI), textual data or numerical data.

The WMD provides analysis of internal and external (both voluntary and involuntary) parameters. In various embodiments, the WMD includes computer and programming that conducts data analysis suitable for use in managing patient health and medical care.

Figure 2:
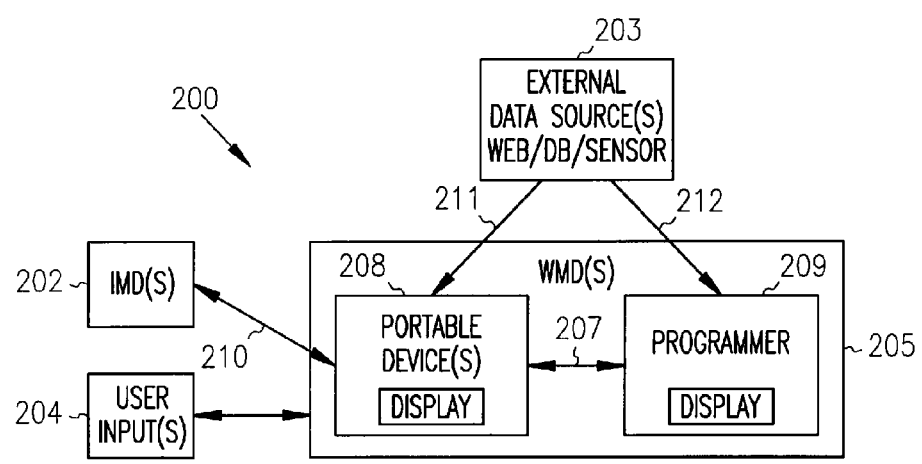
FIG. 2 illustrates an advanced patient management (APM) system according to various embodiments of the present subject matter.

FIG. 2 illustrates an advanced patient management (APM) system according to various embodiments of the present subject matter. Various embodiments of the system 200 include all of the components shown in FIG. 2, various embodiments of the system 200 include less than all of the components shown in FIG. 2, and various embodiments of the system 200 include other components than those shown in FIG. 2.

In the figure, the system 200 is shown to include an IMD 202. In various embodiments, the IMD includes an implantable cardiac device (ICD), cardiac rhythm management (CRM) device, pulse generator, or other implanted medical device that provides therapy to a patient or an organ of a patient, and/or that provides data derived from measurements internal to a patient. In various embodiments, the IMD includes a device to provide drug therapy.

The illustrated system 200 includes at least one WMD 205 that includes at least one display for displaying trended parameters. In the illustrated system, the at least one WMD includes a portable device 208 (such as a PDA) and a programmer 209. The IMD 202 is shown coupled to the portable device 208 by communication link 210. The portable device is further coupled to the programmer by communication link 207. Various embodiments of the present subject matter do not include the portable device 208. In these embodiments, the IMD 202 is able to be coupled directly to the programmer 209 by a communication link (not shown).

At least one external data source 203 (such as web server (s), database(s), and sensor(s)) is coupled to the WMD(s) via at least one communication link. The external data source 203 provides external (with respect to the IMD in the patient) health-related parameters that supplement and/or provide context for the IMD parameters. In the illustrated system, a communication link 211 exists between the portable device 208 and the external data source 203, and a communication link 212 exists between the programmer 209 and the external data source 203. It is noted that various applications may not require both communication links 211 and 212. In the illustration, the system 200 includes at least one user input 204 to the at least one WMD 205. For example, a patient is able to provide health-care information using the portable device 208, and a health care provider is capable of providing healthcare information using the programmer 209.

In various embodiments, the IMD also includes circuitry and programming adapted to monitor the condition and performance of the pulse generator or other IMD. For example, in various embodiments, the IMD provides data concerning the remaining battery condition for a power supply coupled to the IMD. Such data may include information regarding remaining battery capacity or life, battery internal resistance or other measurable parameters. In various embodiments, the data includes information regarding the electrical therapy provided by the IMD. For example, in various embodiments, such data includes lead impedance, sense voltage levels, therapy history, and device therapy mode settings and parameter values. In various embodiments, the IMD provides data regarding dosage, timing and other functions regarding the delivery of a drug therapy or other therapy. For example, in various embodiments, the IMD monitors blood sugar levels and the amount and timing of insulin delivered to the patient.

In various embodiments, the IMD includes a program executing on an internal processor that controls the operation of the IMD. The program instructions reside in a memory accessible to the internal processor. By changing the program, or memory contents, the present system allows the operating program of the IMD to be dynamically tailored to a particular patient or condition. In various embodiments, the operating system, or memory contents of the IMD is changed using wireless communication.

In various embodiments, the IMD includes a wireless transceiver. The transceiver operates using radio frequency transmissions, electromagnetic transmissions, magnetic coupling, inductive coupling, optical coupling, or other means of communicating without need of a wire connection between the IMD and another transceiver.

In various embodiments, the IMD performs a data acquisition function. In various embodiments, the IMD is adapted to monitor a fluid pressure, such as blood or urine. In various embodiments, the detector is adapted to monitor respiration, stress level, or other measurable biometric parameter. In various embodiment, monitoring includes determining an absolute or relative value for a particular biometric parameter. In various embodiments, internal memory within the IMD stores a comparison value which may then be compared with a measured value thereby determining the performance of the IMD or the health of the patient.

In various embodiments, the communication link includes a wireless communication link between the IMD and portable device. The communication link allows communication in one or two directions.

In various embodiments, data from the IMD is communicated to portable device with no data transmitted from portable device to the IMD. In this manner, portable device functions as a data storage facility for the IMD. In various embodiments, data stored in portable device is accessed by a treating physician and used for diagnosis, therapy or other purposes. Programming and controlling the operation of the IMD is performed using a programmer adapted to transmit commands, data or code to the IMD. In various embodiments, portable device executes programming to analyze and process the data received from the IMD. In various embodiments, a communication link precludes transfer of data from portable device to the IMD or precludes transfer of data from the IMD to portable device. For example, it may be desirable in certain circumstances to prevent the portable device from executing programming to automatically adjust the performance or operation of the IMD independent of a programmer.

In various embodiments, data is communicated from portable device to the IMD with no data transmitted from the IMD to portable device. In this manner, portable device functions as an interface to communicate commands, data or code to the IMD. In various embodiments, data is communicated from the IMD to the portable or external device with no data transferred from the device to the IMD.

In various embodiments, data is communicated bidirectionally between the IMD and the portable device. In various embodiments, the communication link between the IMD and the portable device entails a single bidirectional communication channel or includes multiple unidirectional communication channels which, when viewed as a whole, provide bidirectional communication. In various embodiments, a unidirectional communication channel operates using a particular frequency or communication protocol. For example, the link may include a wireless radio frequency link compatible with a transmitter and receiver that uses frequency hopping, spread spectrum technology.

In various embodiments, internal memory within the IMD provides storage for data related to the IMD-provided therapy (such as CRM therapy provided to a heart). For example, the data can relate to the electrical, chemical or mechanical operation of the heart. In addition, the IMD includes memory for programming, comparison and other functions. In various embodiments, the contents of the memory regulates the operation of the IMD.

In various embodiments, the portable device 208 includes or otherwise is incorporated or in communication with a battery operated portable communicator having a processor, memory, and an output interface to communicate with a user and an input interface to receive user entered data. One suitable example of a portable communicator is that of a personal digital assistant (PDA). PDA devices typically include a display screen for presenting visual information to a user and a writing surface for entry of data using a stylus. Data can be entered using a keyboard coupled to the portable communicator or by means of a wired or wireless communication link. Some portable communicator models also include an audio transducer, or sound generator, adapted to produce sounds that are audible by a user. In various embodiment, data from the IMD or the programmer is displayed on a display or screen of the portable device.

In various embodiments, the portable device 208 includes or otherwise is incorporated or in communication with a portable telephone (such as a cellular telephone or a cordless telephone), a pager (one way or two way), or a computer (such as a handheld, palm-top, laptop, or notebook computer) or other such battery operated, processor based, portable communication device.

In various embodiments, the portable device 208 includes data storage and includes programming and instructions to conduct data processing. In various embodiments, the data storage capacity of the portable device 208 augments the data storage capacity of the IMD 202, thus enabling a clinician to access a greater amount of multi-related information regarding the medical condition of a user. For example, but not by way of limitation, the additional information may assist in discovering and understanding relationships among different events.

In various embodiments, a wireless receiver is coupled to a portable device for purposes of receiving data from the IMD 202 through communication link 210. In various embodiments, a wireless transmitter is coupled to the portable device for purposes of transmitting data to the IMD. In various embodiments, a wireless transceiver is coupled to the portable device for purposes of both transmitting data to, and receiving data from, the IMD. In various embodiments, the portable device includes telemetry to facilitate wireless communications.

In various embodiments, circuitry or programming allows the portable device 208 to trigger an alarm under predetermined conditions. In various embodiments, for example, the portable device sounds an audible alarm or transmits an alarm signal if a biometric parameter exceeds a particular value or is outside a specified range of values. The alarm signal can be received by the programmer 209 or a designated physician.

Communication link 207 couples the portable device 208 with the programmer 209. In various embodiments, communication link 207 includes a wired or wireless link that allows data communication between portable device and the programmer. In various embodiments, data is exchanged between portable device and the programmer by means of a removable storage media.

In various embodiments, the programmer 209 includes a processor based apparatus that executes programming to communicate with the IMD 202, the portable device 208, or both. A clinician (e.g. physician) can operate the programmer to communicate with the IMD using 202 portable device as a data interface. In particular, various embodiments provide that data from the IMD 202 can be retrieved by accessing the memory of portable device 208. In various embodiments, the programmer 209 transmits data to the IMD 202 via the portable device 208.

In various embodiments, at least one of the WMDs includes a display. FIG. 2 illustrates a system in which the portable device 208 includes a display and the programmer 209 includes a display. According to various embodiments of the present subject matter, health-related parameters are displayed on the display(s) of the wellness monitoring device(s). In various embodiments, these health-related parameters are acquired via an IMD and/or via an external source such as user input and/or external health data sources such as databases and the like. According to various embodiments of the present subject matter, trended health-related parameters, predetermined events, alerts and/or other information provided in this disclosure are displayed on the wellness monitoring device(s).

Figure 3:
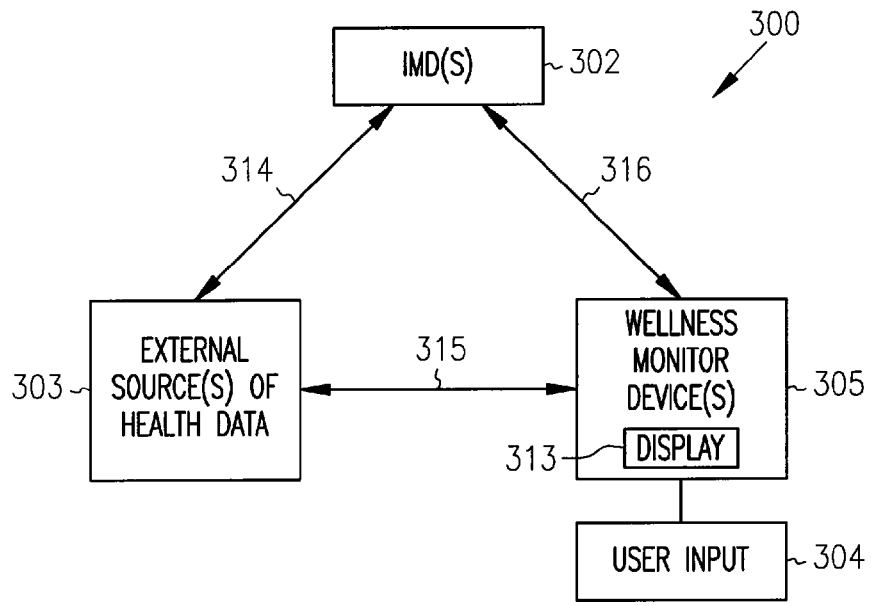
FIG. 3 illustrates an advanced patient management (APM) system having direct communication links according to various embodiments of the present subject matter.

FIG. 3 illustrates an advanced patient management (APM) system having direct communication links according to various embodiments of the present subject matter. According to various embodiments of the system 300, the communication links include wired links, wireless links or both wired and wireless links. Various embodiments include all of the components shown in FIG. 3, various embodiments include less than all of the components shown in FIG. 3, and various embodiments include other components than those shown in FIG. 3.

The illustrated system 300 includes at least one IMD 302, at least one external source of health data 303, and at least one WMD 305 with a display 313. The illustrated system includes a user input 304 to communicate with the WMD. The illustrated system includes a communication link 314 between the IMD(s) 302 and the external source(s) of health-related data 303, a communication link 315 between the external source(s) of health-related data 303 and the WMD(s) 305, and a communication link 316 between the IMD(s) 302 and the WMD(s) 305. It is noted that various embodiments include less than all of the communication links. For example, in various embodiments data from the external source(s) of health data is not communicated to IMD(s) through link 314, and in various embodiments data from the external source(s) of health data is communicated to the wellness monitor device(s) through the IMD(s) and links 314 and 316. Various embodiments implement various communication designs to achieve various data flow.

In various embodiments, the display 313 of the WMD(s) is used to display trended parameters, such as internal parameters from the IMD(s) and external parameters for the external source(s) of health-related data. Other information can be displayed, as is provided throughout the disclosure. Furthermore, a user is able to input additional external health-related information via user input. In various embodiments, the WMD(s) include a portable device such as a PDA, laptop computer, cell phone, and the like. In various embodiments, the WMD(s) include other external devices such as bedside monitors, desktop computers, IMD programmers, and the like.

Figure 4:
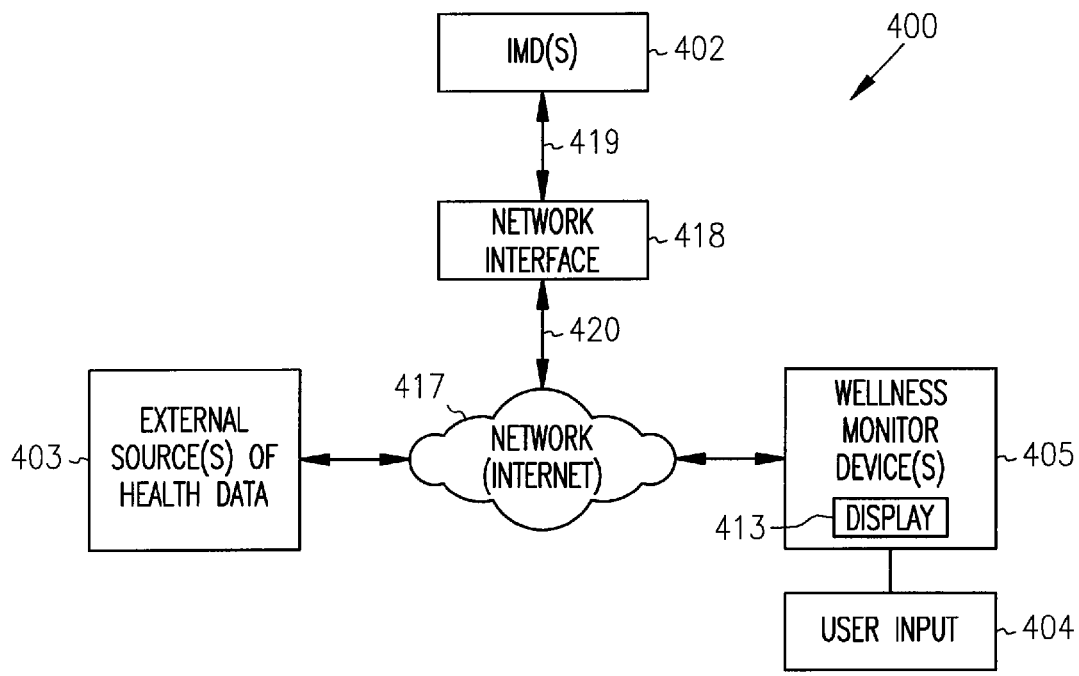
FIG. 4 illustrates an advanced patient management (APM) system having network communication links according to various embodiments of the present subject matter.

FIG. 4 illustrates an advanced patient management (APM) system having network communication links according to various embodiments of the present subject matter. According to various embodiments, the communication links include wired links, wireless links or both wired and wireless links. Various embodiments include all of the components shown in FIG. 4, various embodiments include less than all of the components shown in FIG. 4, and various embodiments include other components than those shown in FIG. 4.

The illustrated system 400 includes at least one IMD 402, at least one external source of health data 403, at least one WMD 405 with a display 413, and at least one network infrastructure through which the other devices (also referred to within this discussion as network devices) are capable of communicating. The illustrated system includes a user input 404 to communicate with the WMD 405. In various embodiments, the WMD(s) includes a portable device such as a PDA, laptop computer, cell phone, and the like. In various embodiments, the wellness monitor device(s) include other external devices such as bedside monitors, desktop computers, IMD programmers, and the like. Examples of a network communication link includes, but is not limited to, one or more of the following: cellular telephone coupled to a portable device via the Internet, a private area branch exchange (PABX, also known as a PBX); an intranet network; an ethernet connection or other remote communication means.

The illustrated system includes a communication link between the IMD(s) 402 and the external source(s) of health-related data 403 via the network 417, a communication link between the external source(s) of health-related data 403 and the WMD(s) 405 via the network 417, and a communication link between the IMD(s) and the WMD(s) 405 via the network 417. The illustrated system includes a network interface or adapter 418. The network adapter 418 wirelessly communicates with the IMD 402 via communication link 419, and communicates with network devices through network via communication link 420. Although not expressly, other network devices include a network interface.

Various embodiments include a direction communication link as illustrated in FIG. 3 and a network communication link as illustrated in FIG. 4. The display of the WMD(s) is used to display trended parameters, such as internal health-related parameters from the IMD(s) and external health-related parameters for the external source(s) of health-related data. Furthermore, a user is able to input additional external health-related information via user input.

Figure 5:
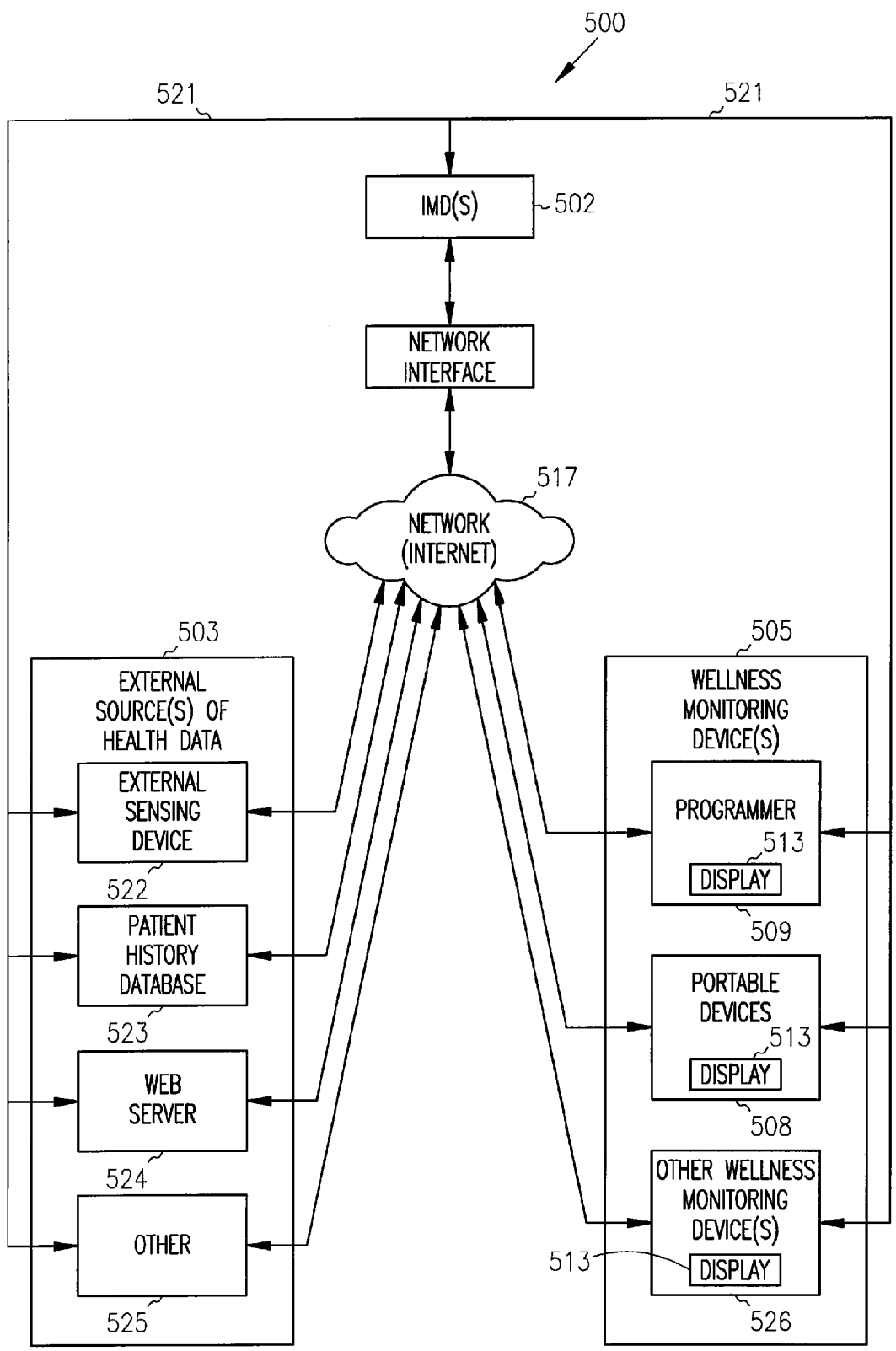
FIG. 5 illustrates an advanced patient management (APM) system having network communication links according to various embodiments of the present subject matter.

FIG. 5 illustrates an advanced patient management (APM) system having network communication links according to various embodiments of the present subject matter. Various embodiments include all of the components shown in FIG. 5, various embodiments include less than all of the components shown in FIG. 5, and various embodiments include other components than those shown in FIG. 5.

The illustrated system 500 includes at least one IMD 502, at least one external source of health data 503, at least one WMD 505 with a display 513, and at least one network infrastructure 517 through which the other devices (also referred to within this discussion as network devices) are capable of communicating. The illustrated system 500 also includes direct communication connections 521 between the IMD(s) 502 and the external source(s) of the health data 503, and between the WMD(s) 505 and the IMDS(s) 502. One of ordinary skill in the art will understand, upon reading and comprehending this disclosure, that various embodiments include some direct communication connections between some components and include some network communication connections between some components.

The illustrated external source(s) of health data 503 include at least one external sensing device 522 such as a body temperature or blood pressure monitor, at least one patient history database 523, at least one web server 524, and other external sources 525. Various embodiments of the present subject matter include one or more of the illustrated external sources of health data. The illustrated WMD(s) includes a programmer 509 with a display, a portable device 508 (such as a PDA or laptop computer) with a display, or other WMD(s) 526 with a display. Various embodiments of the present subject matter include one or more of the illustrated WMDs.

Figure 6:
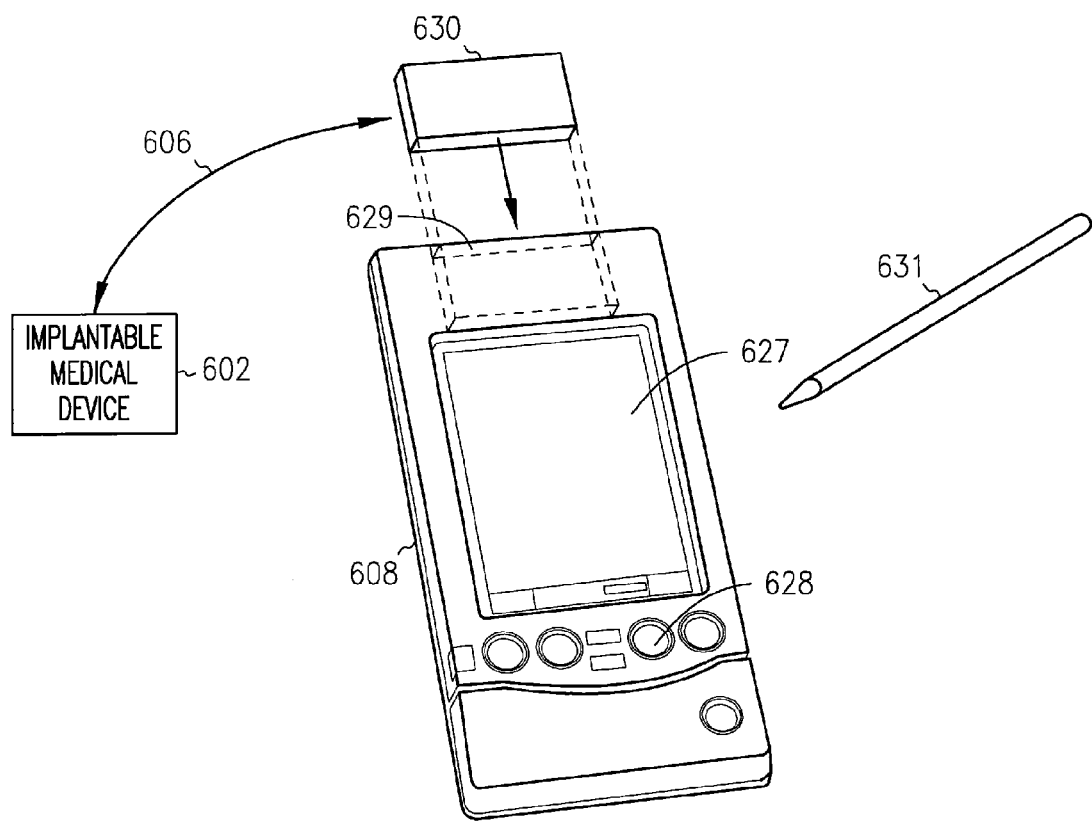
FIG. 6 illustrates a perspective view of an advanced patient management (APM) system that includes an IMD and a portable device such as a PDA.

FIG. 6 illustrates a perspective view of an advanced patient management (APM) system that includes an IMD 602 and a portable device 608 such as a PDA. The illustrated portable device 608 includes a display screen 627, a plurality of user operable buttons 628, and an expansion port 629 which receives and is coupled to an expansion device 630 that is designed to communicate with the IMD 602. In various embodiments, a specially designed portable device is employed with an integrated communication subsystem. A stylus 631 can be used to manually enter data using screen. Link 606 is illustrated as a bidirectional link and thus, data from IMD 602 is wirelessly telemetered to the portable device 608 through the expansion device 630. In addition, data, or programming from the portable device 608 is wirelessly telemetered from the expansion device 630 to the IMD 602.

According to various embodiments, the portable device (such as the illustrated PDA) generates a prompt at various times calling for a response in the form of a user input. A user may enter data using any of a variety of means. For example, a response may be entered using stylus, buttons, or an external keyboard. In one embodiment, portable device responds to voice commands received from a user. A prompt may be visually displayed using screen or audibly generated using an internal sound generator. Manually entered data received from a user, as well as data received from other inputs is stored using the portable device. The data stored in the portable device is available for processing, and to tailor the therapy.

In addition to data entry, the portable device 608 provides a user with limited control over the operation of an IMD 602 in various embodiments. In various embodiments, reasonable constraints on the authority to change the operation of IMD are established and implemented by a clinician.

Figure 7:
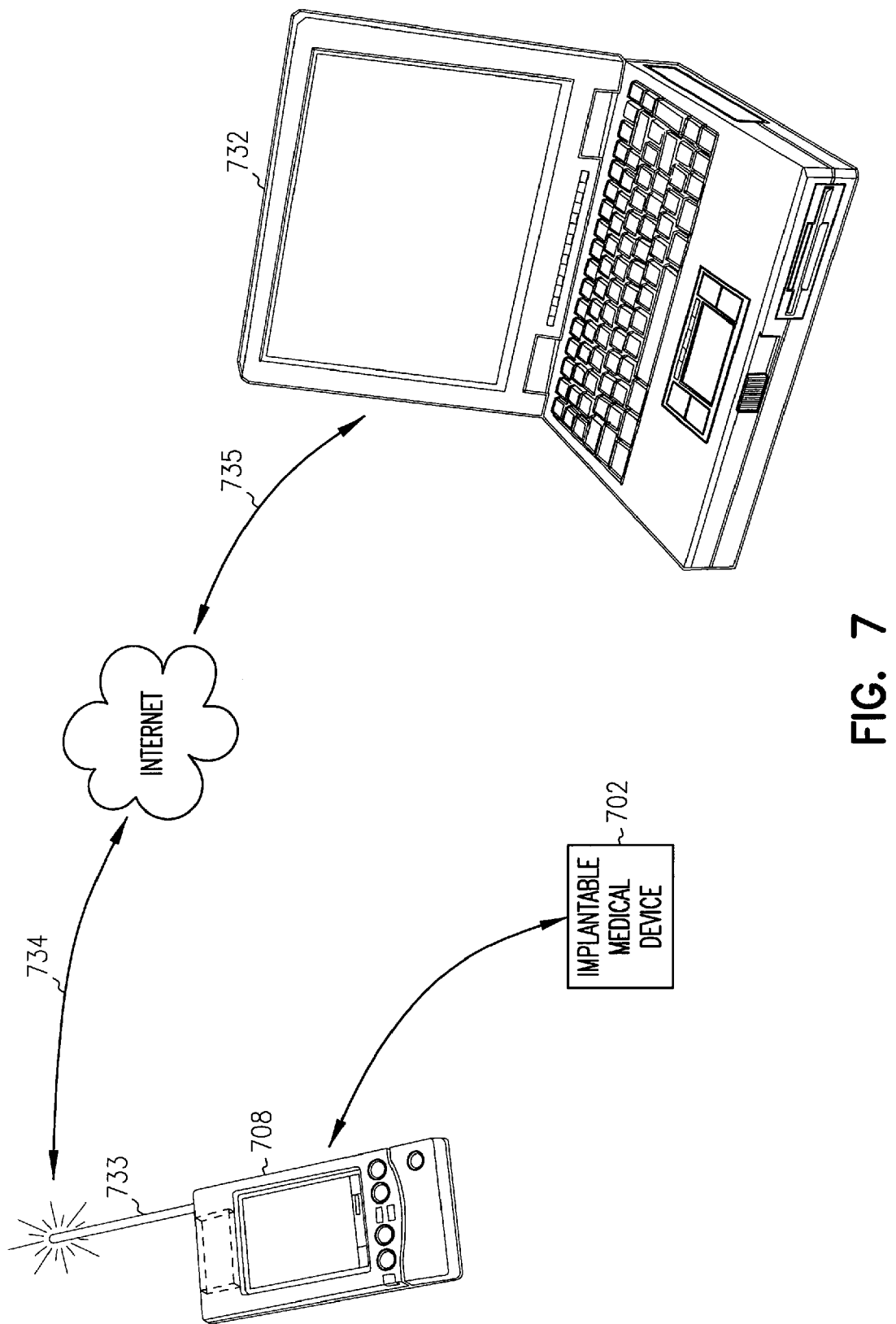
FIG. 7 illustrates a perspective view of an advanced patient management (APM) system that includes an IMD, a portable device such as a PDA, and another wellness monitoring device, such as a programmer for the IMD, networked to the PDA.

FIG. 7 illustrates a perspective view of an advanced patient management (APM) system that includes an IMD 702, a portable device 708 such as a PDA, and another WMD 732, such as a programmer for the IMD, networked to the PDA. The illustrated portable device includes a wireless communication antenna 733. In various embodiments, the portable device 708 is adapted for wireless access to Internet network using link 734. In various embodiments, link 734 includes a radio frequency communication link. The programmer accesses the Internet via link 735. In various embodiments, 735 link includes a dial-up modem connection, a cable modem connection, a DSL connection, an ISDN line, or other channel providing access to the Internet.

A user is able to compile contextual information regarding IMD 702, as well as himself, using the portable device 708. In various embodiments, a clinician using the programmer 732 is able to remotely access the data stored in the portable device 708 using link 735, Internet and link 734. In this manner, programmer 732 is able to wirelessly receive the data, process the data, and transmit data and code to change the future operation of the IMD 702.

Figure 8:
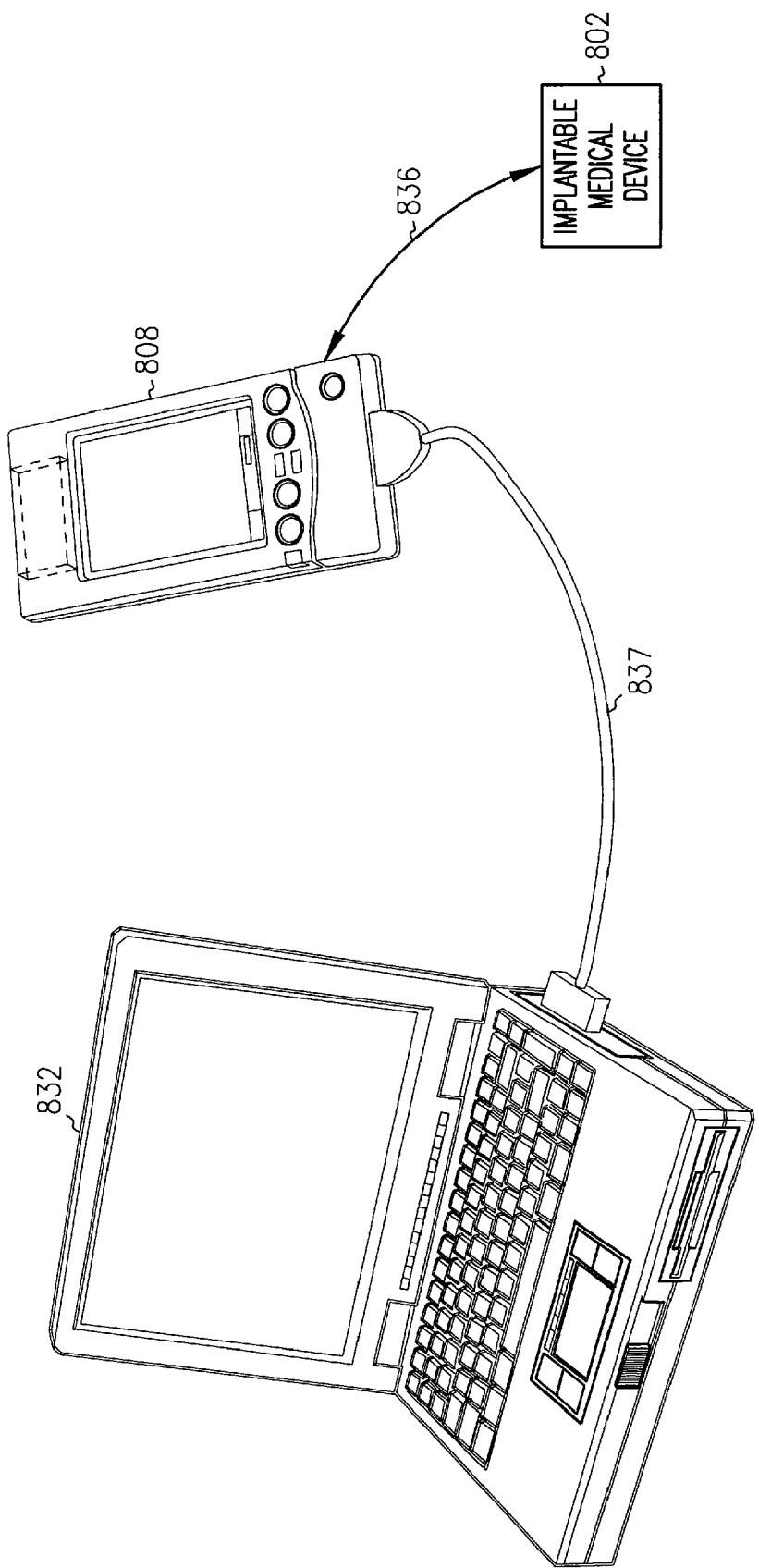
FIG. 8 illustrates a perspective view of an advanced patient management (APM) system that includes an IMD, a portable device such as a PDA, and another wellness monitoring device, such as a programmer for the IMD, directly connected to the PDA.

FIG. 8 illustrates a perspective view of an advanced patient management (APM) system that includes an IMD 802, a portable device such as a PDA 808, and another WMD 832, such as a programmer for the IMD, directly connected to the PDA. The PDA is coupled to IMD by wireless link 836, and is further coupled to programmer by link 837 (illustrated as a communication cable).

A clinician operating programmer 832 is able to exchange data or code with the PDA 808 using link 837. Connector is a multi-conductor connector providing access to data of the PDA. It will be appreciated that link may couple the PDA to a local area network or other communication network. For example, the PDA may be connected to a public switched telephone network (PSTN) link, and thus, programmer may exchange data with portable communicator using a modem coupled to PSTN.

Figure 9:
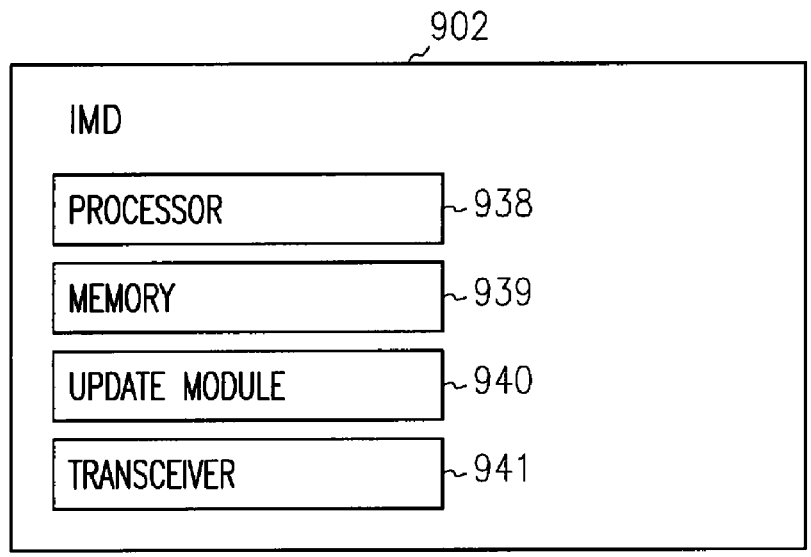
FIG. 9 illustrates a block diagram of an IMD according to various embodiments of the present subject matter.

FIG. 9 illustrates a block diagram of an IMD according to various embodiments of the present subject matter. The illustrated IMD 902 includes a processor 938, memory 939, an update module 940 and a transceiver 941. In operation, the processor governs the operation of IMD and executes programming stored in memory. In addition to the executable program, memory also includes data storage regarding the patient and IMD. The update module operates in conjunction with processor, memory and transceiver to receive, install, and execute new instructions for execution by processor.

Figure 10:
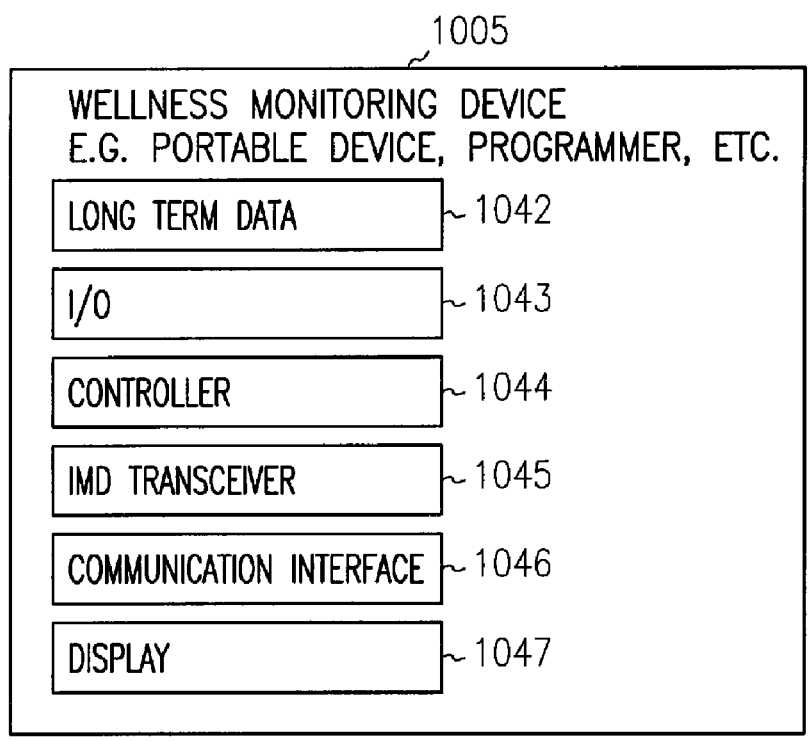
FIG. 10 illustrates a block diagram of a wellness monitoring device, such as a portable device, according to various embodiments of the present subject matter.

FIG. 10 illustrates a block diagram of a WMD, such as a portable device, a programmer and the like, according to various embodiments of the present subject matter. The illustrated WMD 1005 includes long term data storage 1042, an input/output 1043, a controller 1044, an IMD transceiver 1045, a communication interface 1046 and a display 1047. The long term data storage augments the data storage capacity of the memory of the IMD. In various embodiments, the storage is of a greater capacity than that of memory, is physically larger in size, and is less expensive and more robust than medical grade implantable memory.

The input/output, the IMD transceiver and the communication interface, in conjunction with the controller enables receipt and transmission of data from the IMD as well as data from other sources such as other WMDs, databases and the like. The IMD transceiver provides a wireless communication link between the IMD and the portable device. The display is used to, among other things, display parameters that have been acquired and trended by the system according to the present subject matter.

Figure 11:
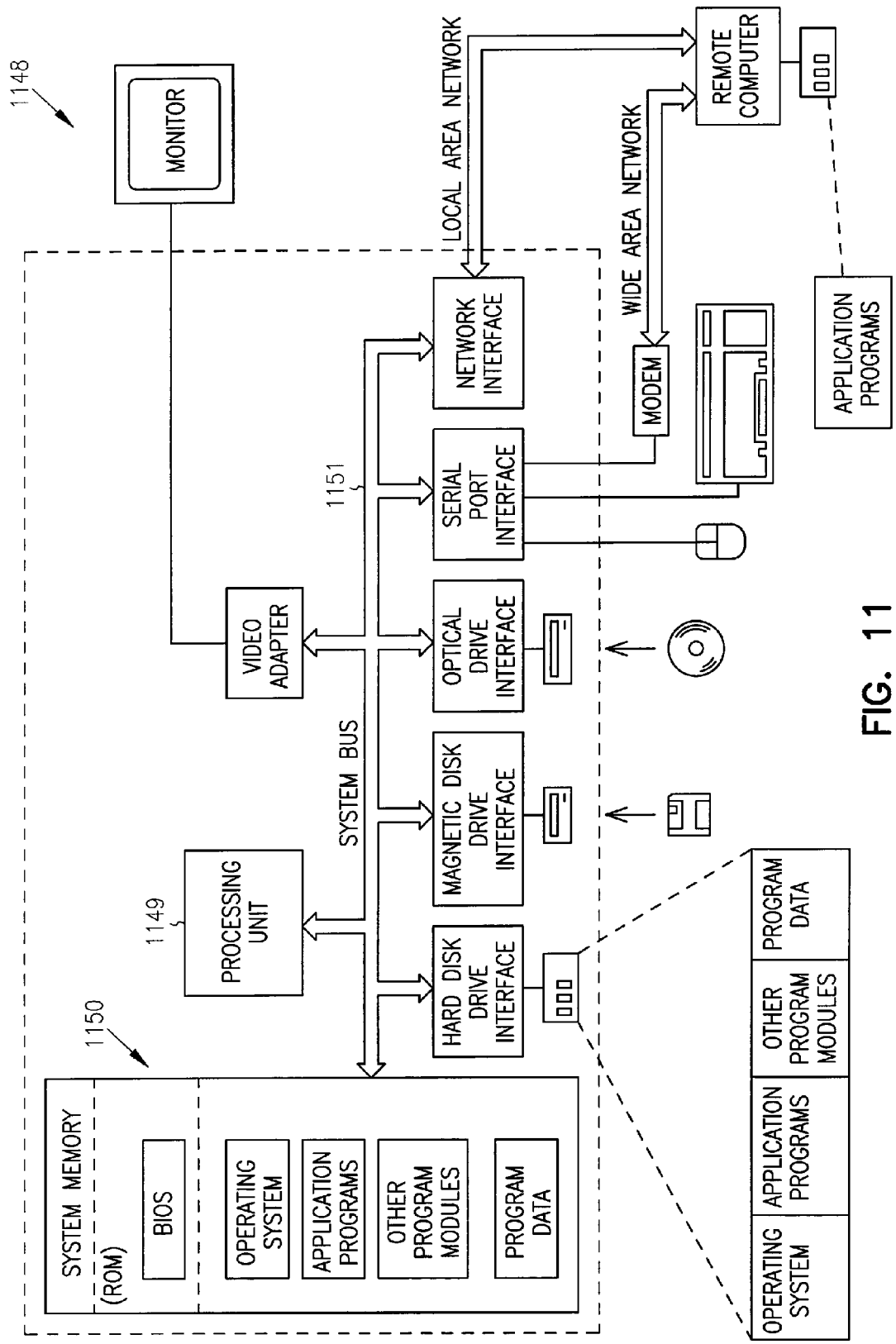
FIG. 11 illustrates various embodiments of a wellness monitoring device (WMD) in the form of a general-purpose computing device.

FIG. 11 provides a brief, general description of a suitable computing environment in which the above embodiments may be implemented. The illustrated computing environment, or portions thereof, can be implemented in a WMD. Additionally, portions of the illustrated computing environment (such as the system memory and processor) can be implemented in IMDs.

Embodiments of the present subject matter can be described in the general context of computer-executable program modules containing instructions executed by a computing device. The term module includes hardware, firmware, software, and various combinations thereof to perform task(s) described in this disclosure, as is understood by one of ordinary skill in the art upon reading and comprehending this disclosure. Program modules include routines, programs, objects, components, data structures, etc. that perform particular tasks or implement particular abstract data types. Those skilled in the art will appreciate that the invention may be practiced with other computer-system configurations, including hand-held devices, multiprocessor systems, microprocessor-based programmable consumer electronics, network PCs, minicomputers, mainframe computers, and the like which have multimedia capabilities. The invention may also be practiced in distributed computing environments where tasks are performed by remote processing devices linked through a communications network. In a distributed computing environment, program modules may be located in both local and remote memory storage devices.

FIG. 11 illustrates various embodiments of a WMD in the form of a general-purpose computing device. One of ordinary skill in the art will understand, upon reading and comprehending this disclosure, how to implement the present subject matter using other WMDs and IMDs with some of the illustrated components or other components.

The illustrated computing device 1148 includes a processing unit 1149, a system memory 1150, and a system bus 1151 that couples the system memory and other system components to processing unit. The system bus may be any of several types, including a memory bus or memory controller, a peripheral bus, and a local bus, and may use any of a variety of bus structures. The system memory includes read-only memory (ROM) and random-access memory (RAM). A basic input/output system (BIOS), stored in ROM, contains the basic routines that transfer information between components of personal computer. BIOS also contains start-up routines for the system. Various embodiments of the computing device further include a hard disk drive for reading from and writing to a hard disk (not shown), a magnetic disk drive for reading from and writing to a removable magnetic disk, and an optical disk drive for reading from and writing to a removable optical disk such as a CD-ROM or other optical medium. Hard disk drive, magnetic disk drive, and optical disk drive are connected to system bus by a hard-disk drive interface, a magnetic-disk drive interface, and an optical-drive interface, respectively. The drives and their associated computer-readable media provide nonvolatile storage of computer-readable instructions, data structures, program modules and other data for the computing device. Those skilled in the art will appreciate that other types of computer-readable media which can store data accessible by a computer may also be used.

Program modules can be stored on the hard disk, magnetic disk, optical disk, ROM and RAM. Program modules may include operating system, one or more application programs, other program modules, and program data. A user may enter commands and information into personal computer through input devices such as a keyboard and a pointing device. These and other input devices are often connected to the processing unit through a serial-port interface coupled to system bus; but they may be connected through other interfaces not shown in FIG. 11, such as a parallel port or a universal serial bus (USB). A monitor or other display device also connects to system bus via an interface such as a video adapter. In addition to the monitor, personal computers typically include other peripheral output devices (not shown) such as speakers and printers. In one embodiment, one or more speakers or other audio output transducers are driven by sound adapter connected to system bus.

In various embodiments the computing device operates in a networked environment using logical connections to one or more remote devices such as remote computer. Examples of remote computers include a personal computer (PC), a server, a router, a network PC, a peer device, or other common network node. In various embodiments, the remote computer includes many or all of the components described above in connection with the computing device; however, only a storage device is illustrated in FIG. 11 to simplify the disclosure. The logical connections depicted in FIG. 11 include local-area network (LAN) and a wide-area network (WAN). Such networking environments exist in offices, enterprise-wide computer networks, intranets and the Internet. The computing device connects to local network through a network interface or adapter in various embodiments, and to a WAN/Internet network through a modem or other means for establishing communications over network.

Various embodiments of the present subject matter are illustrated in FIGS. 12-27 and are discussed below. One of ordinary skill in the art will understand, upon reading and comprehending this disclosure, that these embodiments are not necessarily mutually exclusive as various embodiment can be combined or otherwise modified to create other embodiments. One of ordinary skill in the art also will understand, upon reading and comprehending this disclosure, that various elements shown and described with respect to one or more of FIGS. 1-11 are capable of being combined with various elements shown and described with respect to one or more of FIGS. 12-27.

Acquisition, Trending and Displaying Health-Related Parameters

FIGS. 12-16 illustrate various embodiments of the present subject matter related to acquiring, trending and displaying health-related parameters. In various embodiments, an IMD acquires, trends and displays a variety of parameters pertinent to the health status of a patient.

Figure 12:
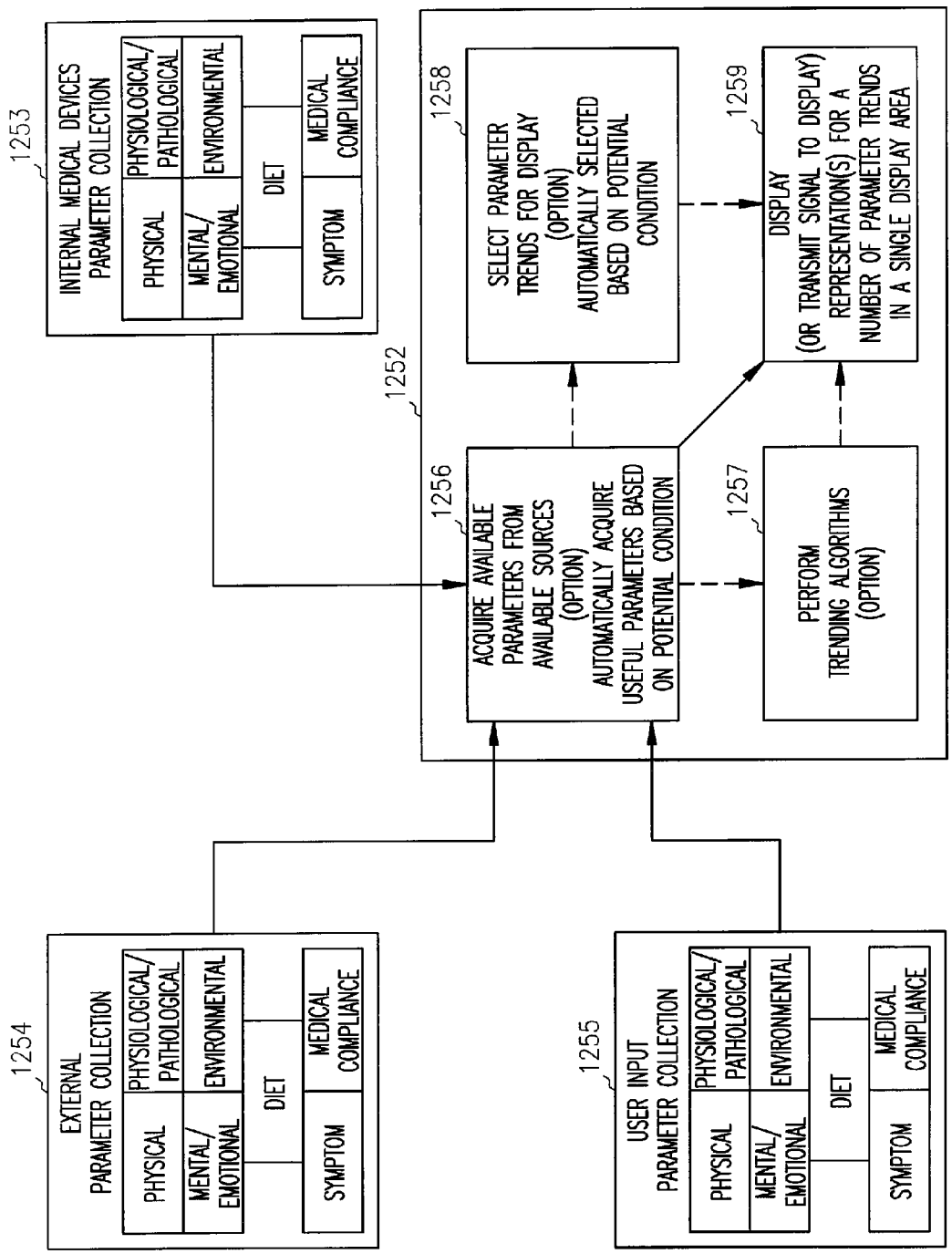
FIG. 12 illustrates a block diagram of an advanced patient management system for acquiring, trending and displaying multiple health-related parameters according to various embodiments of the present subject matter.

FIG. 12 illustrates a block diagram of a device for acquiring, trending and displaying multiple health-related parameters according to various embodiments of the present subject matter. The device 1252 acquires available parameters from available sources. In various embodiments, the device 1252 includes a WMD such as a portable device, a programmer and the like. In various embodiments, the device 1252 includes an IMD. For example, potentially available sources include an IMD parameter collection 1253 (internal health-related parameters such as internal physiological measurements, applied therapy, device performance, and the like), an external parameter collection 1254 (external parameters such as external physiological and environmental measurements, databases, and the like), and a user input parameter collection 1255 (voluntary data). User inputs can be considered to be an external health-related parameter. However, for purposes of the description with respect to FIG. 12, external parameter collection and user input parameter collection are considered separately.

In various embodiments, the IMD parameter collection 1253 includes at least one of a physical parameter type, a physiological/pathological parameter type, a mental/emotional parameter type, a diet parameter type, an environmental parameter type, a symptom parameter type, and a medical compliance type. In various embodiments, the IMD is gathers information from an external device or sensor in order to gather certain parameter types. Furthermore, the IMD is capable of acquiring medication compliance by monitoring a measurable parameter correlated to compliance. For example, blood pressure is monitored to verify that a patient is compliant with hypertensive medications. The IMD is also capable of acquiring environmental data, such as barometric pressure using an implanted pressure sensor and such as relative temperature changes using an implanted temperature sensor near the surface of the skin.

One definition of mental is of or relating to the mind. One definition of emotional is relating to or marked by an emotion (a strong feeling, aroused mental state, or intense state of drive or unrest, which may be directed toward a definite object and is evidenced in both behavior and in psychologic changes, with accompanying autonomic nervous system manifestations). One definition of physiological is normal, as opposed to pathologic. One definition of pathological is diseased. Other definitions can be used consistently with respect to these terms.

In various embodiments, the external parameter collection 1254 includes one or more of a mental/emotional parameter type, an environmental parameter type and a diet parameter type. In various embodiments, the external parameter collection 1254 includes a physical parameter type, a physiological/pathological parameter type, a symptom parameter type, and/or a medication compliance parameter type. The external parameter collection can include any one or any combination of the above parameter types according to embodiments of the present subject matter.

In various embodiments, the user input parameter collection 1255 includes one or more of a mental/emotional parameter type, an environmental parameter type and a diet parameter type. In various embodiments, the user input parameter collection 1255 includes a physical parameter type, a physiological/pathological parameter type, a symptom parameter type, and/or a medication compliance parameter type. The user input parameter collection can include any one or any combination of the above parameter types according to embodiments of the present subject matter.

Examples of a physical parameter type include, but are not limited to, parameters related to activity, posture, and sleep. Examples of a mental/emotional parameter type include, but are not limited to, parameters related to stress, excitement, anger, anxiety (such as may be detected via sighing), and depression. Examples of physiological/pathological parameter types include, but are not limited to, parameters related to blood pressure, respiration rate and patterns, and medical test results. Examples of environmental parameter types include, but are not limited to, parameters related to altitude, temperature, air quality, pollen count, and humidity. Examples of diet parameter types include, but are not limited to, parameters related to sodium intake, fluid intake and lipid intake. Examples of symptom parameter types include, but are not limited to, parameters related to pain, dyspnea and fatigue. In various embodiments, a symptom can be considered to be, for example, a patient-perceived condition based on frequency, severity and/or repetition. Examples of medication compliance parameter types include, but are not limited to, parameters related to drug administration such as drug type, dosage and time. Examples of drug type includes insulin, beta-blockers, diuretics and the like.

Health-related parameters are acquired from various sources. In various embodiments, a number of parameters are acquired from IMD, and from external sources such as external parameter collections (programmer, web servers, patient databases, external sensors, etc.) and user input parameter collections (answered questions, etc.). The parameter trends are displayed in a single display area of at least one of the WMDs.

In various embodiments, available parameters are acquired at module 1256. The acquired parameters are processed according to a procedure implemented in software. In various embodiments, the software automatically acquires those health-related parameters deemed to be useful based on a potential health condition. In various embodiments, the software instructions provide a procedure, when operated on by a processor, which automatically determines a potential health condition, and thus additional parameters to be acquired, from previously acquired parameters. Thus, the present subject matter is capable of automatically and intelligently acquiring additional parameters to confirm and/or dismiss an initial diagnosis.

In various embodiments, module 1257 includes software instructions that, when operated on by a processor, provide a procedure that automatically trends the acquired parameters. The trending procedure analyzes the parameters as a function of time or other measured parameter. In various embodiments, module 1258 allows a user to select parameter trends to be displayed in a single display area. Module 1259 is used to display representations in a single display area. In various embodiments in which device 1252 includes a WMD, module 1259 displays the representation on a display of the WMD. In various embodiments in which device 1259 includes an IMD, module 1259 transmits a signal for reception by a display device to display the representation on the display device.

In various embodiments, the acquired data and trends are analyzed to select an updated program or specify updated operational parameters for the IMD. The updated program or operational parameters are capable of being transferred and implemented by IMD.

Figure 13:
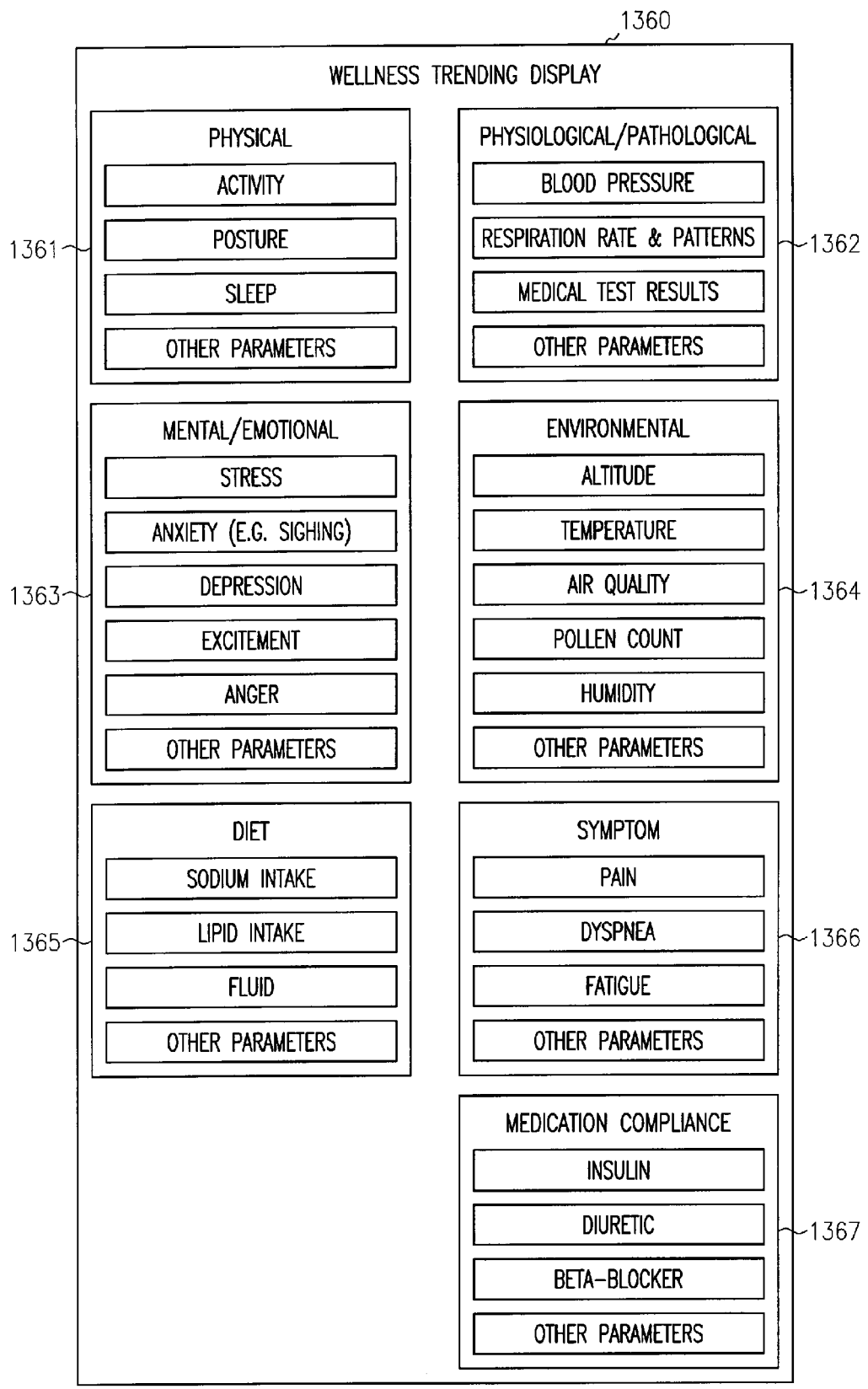
FIG. 13 illustrates a block diagram of a wellness trending display generally illustrating parameter trends available for display according to various embodiments of the present subject matter.

FIG. 13 illustrates a block diagram of a wellness trending display generally illustrating parameter trends available for display according to various embodiments of the present subject matter. In various embodiments of the display 1360, trends associated with at least one of a physical parameter type 1361, a physiological/pathological parameter type 1362, a mental/emotional parameter type 1363, an environmental parameter type 1364, a diet parameter type 1365, a symptom parameter type 1366 and a medication compliance parameter type 1367 (and various combinations of a physical parameter type, a physiological/pathological parameter type, a mental/emotional parameter type, an environmental parameter type, a diet parameter type, a symptom parameter type and a medication compliance parameter type) are available to be displayed in a single wellness trending display area 1360.

In various embodiments, parameters available to be displayed that are associated with a physical parameter type include, but are not limited to, parameters related to activity, posture, and sleep. In various embodiments, parameters available to be displayed that are associated with a mental/emotional parameter type include, but are not limited to, parameters related to stress, anxiety (such as may be detected via sighing), excitement, anger and depression. In various embodiments, parameters available to be displayed that are associated with a physiological/pathological parameter type include, but are not limited to, parameters related to blood pressure, respiration rate and patterns, and medical test results. In various embodiments, parameters available to be displayed that are associated with a environmental parameter type include, but are not limited to, parameters related to altitude, temperature, air quality, pollen count and humidity. In various embodiments, parameters available to be displayed that are associated with a diet parameter type include, but are not limited to, parameters related to sodium intake, fluid intake and lipid intake.

Figure 14:
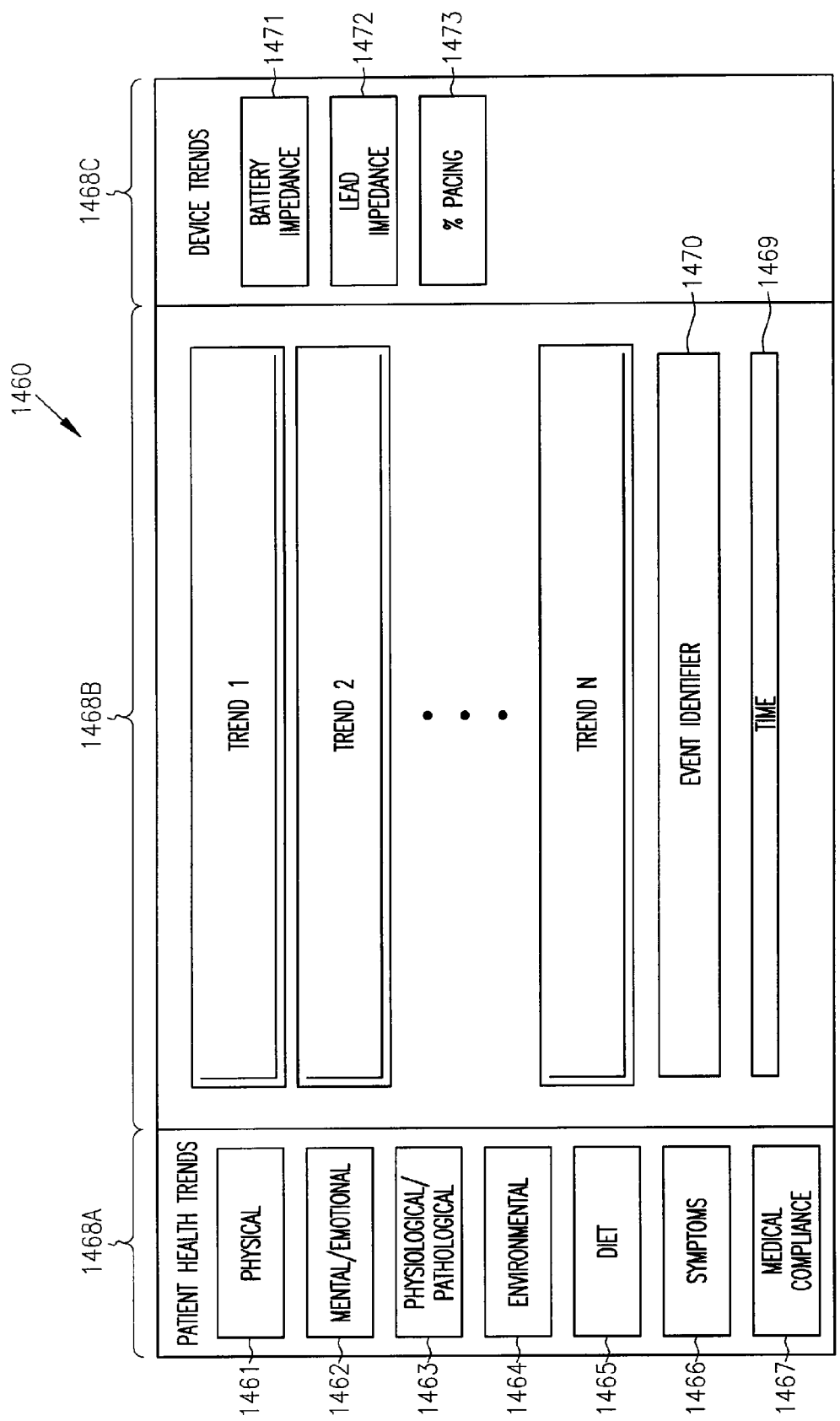
FIG. 14 illustrates a block diagram of a wellness trending display illustrating an arrangement for selecting and displaying parameter trends according to various embodiments of the present subject matter.

FIG. 14 illustrates a block diagram of a wellness trending display illustrating an arrangement for selecting and displaying parameter trends according to various embodiments of the present subject matter. In the illustrated embodiment, the screen display 1460 of the WMD includes a patient health trend area 1468A, a device trend area 1468B, and a trend display area 1468C. In various embodiments, the screen display includes a time indicator 1469 and an event identifier 1470. The event identifier is used to display predetermined events. In various embodiments, significant events include events that are clinically important in themselves, those events that may trigger clinically important changes, and/or those events that explain clinically important changes. The illustrated screen display promotes the correlation of various parameter trends to various predetermined events. The correlation of various parameter trends is useful to diagnose and treat various health conditions.

In various embodiments, various trended parameters from the patient health trend area and from the device trend area are capable of being displayed in the trend display area. In various embodiments, a user is capable of selecting the displayed parameters and/or is capable of modifying the scale, arrangement and/or other display characteristic.

The illustrated patient health trend area 1468A includes a physical parameter type 1461, a physiological/pathological parameter type 1462, a mental/emotional parameter type 1463, an environmental parameter type 1464, a diet parameter type 1465, a symptom parameter type 1466 and a medication condition parameter type 1467. In various embodiments, selecting the parameter type displays a second window for selecting a particular parameter associated with that parameter type. For example, selecting the physical parameter type button displays available physical parameters for display such as activity, posture and sleep. Other embodiments provide other ways for a user to select the parameters to be displayed.

The illustrated device trend area 1468C includes parameters associated with the device that can affect the sensed parameters or that otherwise provide context to the sensed parameters. In various embodiments of the present subject matter which include a pulse generator IMD, the device trend area includes battery impedance 1471, lead impedance 1472, and percent pacing 1473. One of ordinary skill in the art will understand, upon reading and comprehending this disclosure, the significance of device trends such as battery impedance, lead impedance, percent pacing and the like. One of ordinary skill in the art will further understand, upon reading and comprehending this disclosure, the desirability of correlating device trends with the patient health trends.

A number of parameters trends, shown as trend 1, trend 2 . . . trend n, are capable of being displayed in the trend display area 1468B. The trends are plotted as a function of time, which is illustrated at 1469. In various embodiments, and event identifier, represented at 1470, is also displayed in the trend display area. The event identifier displays predetermined events that occurred at various times, and assists with determining causes for changes in the displayed parameter trends.

Figure 15:
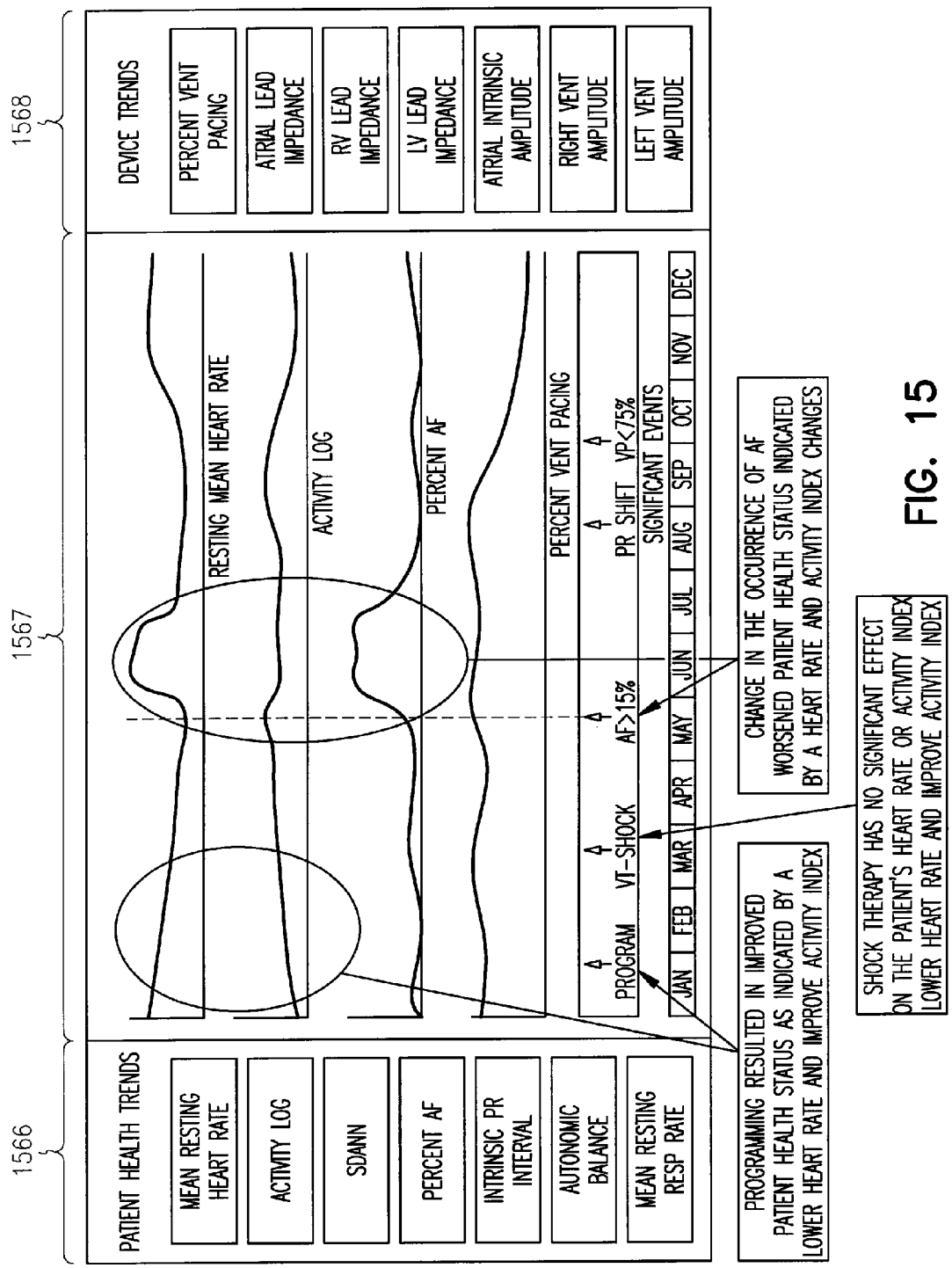
FIG. 15 illustrates an example of a wellness trending display.

FIG. 15 illustrates an example of a wellness trending display. In the illustrated embodiment, the screen display of the wellness monitor device includes a patient health trend area 1566, a device trend area 1568, and a trend display area 1567.

In the illustrated embodiment, a number of patient health parameter trends are accessible in the patient health trend area, including mean resting heart rate trends, an activity trends, standard deviation of averaged normal-to-normal (SDANN) interval trends, percent atrial fibrillation (AF) trends, intrinsic PR interval trends (the period of time from the onset of the P wave (atrial depolarization) to the onset of the QRS complex (ventricular depolarization)), autonomic balance trends, and mean resting respiratory trends.

SDANN is a particular measure of heart rate variability (HRV) that is based on 24 hour recordings of heartbeats. SDANN is computed by determining average heart rate over a given interval (e.g five (5) minute intervals), and taking the standard deviation of the heart rates. Preferably, the SDANN measure uses every interval during the day assuming that all of the intervals provide good recordings. For example, there are 288 5-minute periods during a day. If all of the intervals provide good recordings, the SDANN is the standard deviation of these 288 averages. However, since all of the recordings may not be good throughout the 24 hour day, the SDANN is computed from the good portions of the recording.

Upon reading and understanding this disclosure, those skilled in the art will readily understand the value of the heart rate, percent atrial fibrillation, autonomic balance, and respiratory trends in the context of patient wellness. The intrinsic PR interval is useful to determine optimal cardiac resynchronization therapy in heart failure patients.

In the illustrated embodiment, a number of device trends 1568 are accessible in the device trend area, including percent ventricular pacing trends, atrial lead impedance trends, RV lead impedance trends, LV lead impedance trends, atrial intrinsic amplitude trends, right ventricular amplitude trends, and left ventricular amplitude trends. Upon reading and comprehending this disclosure, those skilled in the art will readily understand the value of the parameters in assessing device functionality and thereby the ability of the device to deliver proper therapy.

Labels are provided in FIG. 15 to illustrate the correlation between various parameter trends and various predetermined events. For example, programming the IMD, as indicated by the event identifier, resulted in a lower resting mean heart rate and an increased activity. U.S. Pat. No. 6,021,351, issued to Kadhiresan et al. and entitled Method and Apparatus For Assessing Patient Well-Being, describes an example of an activity. U.S. Pat. No. 6,021,351 is assigned to Applicant's assignee, and is hereby incorporated by reference in its entirety. The illustration also shows that a ventricular tachycardia (VT) shock therapy did not significantly affect the heart rate or activity, but that atrial fibrillation (AF>15%) significantly worsened the patient's health status as indicated by an increased resting mean heart rate and a decreased activity. One of ordinary skill in the art will understand, upon reading and comprehending this disclosure, that other parameters and predetermined events can be acquired and displayed to illustrate the correlation between various parameter trends and various predetermined events.

Figure 16:
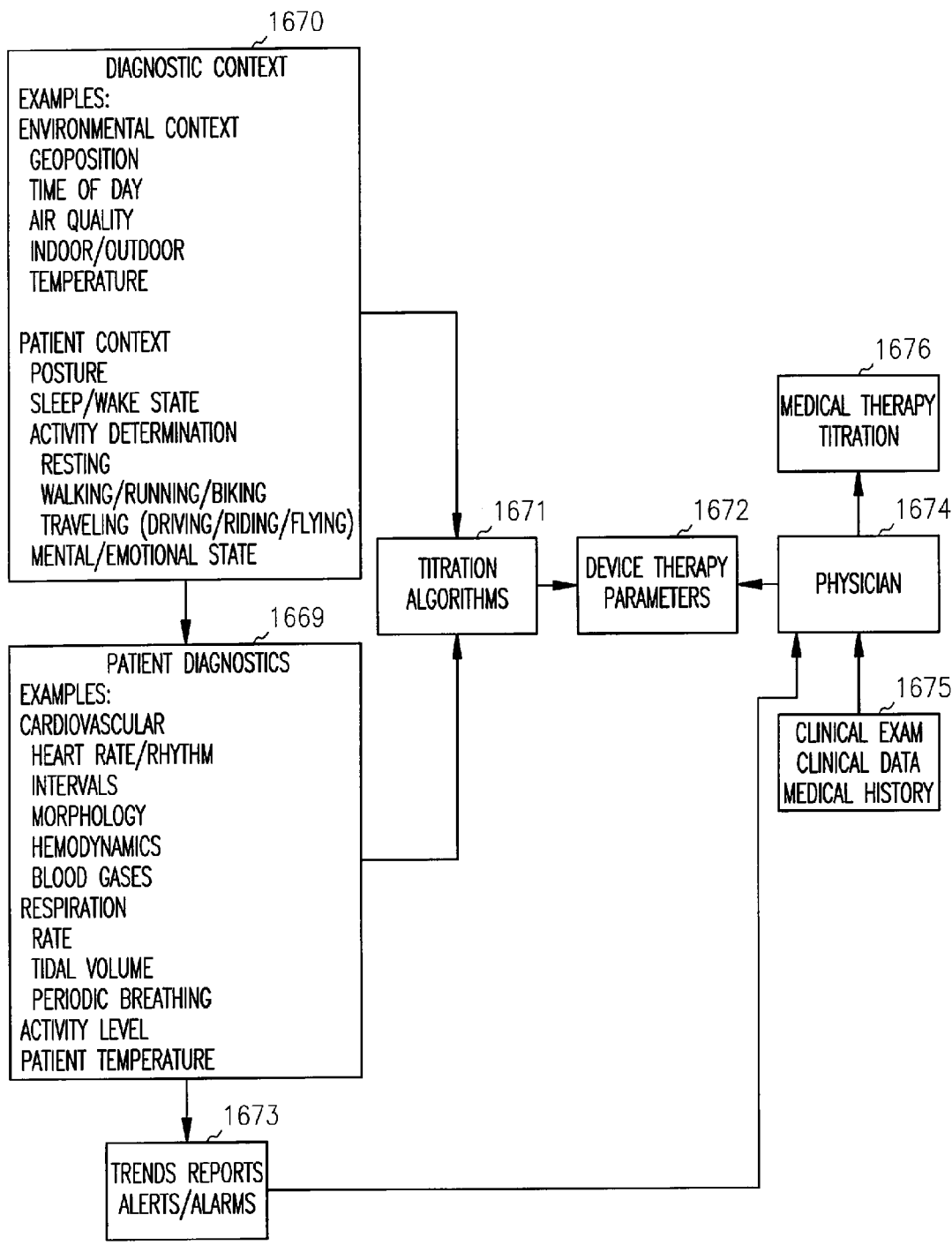
FIG. 16 illustrates a block diagram according to various aspects of the present subject matter in which a diagnostic context is provided to assist with interpreting the health condition of the patient, and to appropriately adjust the device and/or medical therapy, accordingly.

FIG. 16 illustrates a block diagram according to various aspects of the present subject matter in which a diagnostic context is provided to assist with interpreting the health condition of the patient, and to appropriately adjust the device and/or medical therapy, accordingly. The patient diagnostics 1669 and the diagnostic context 1670 are capable of being acquired using a variety of IMD and external sources, such as those provided throughout this disclosure. A number of patient diagnostics and diagnostic contexts are provided in FIG. 15, and will not be repeated in this specification.

In the illustrated embodiment, the diagnostic context 1670 is used as an input in forming the patient diagnosis 1669. The diagnostic context and the patient diagnostics provide inputs to titration algorithms 1671, which are used to determine an appropriate device therapy based on the diagnosis and the context of the diagnosis. The titrated settings for the device therapy are implemented by the device at 1672. At 1673, various trends, reports and/or alerts/alarms are determined based on the patient diagnostics. A physician 1674 receives these various trends, reports and/or alerts/alarms, along with other data 1675 such as clinical exams, clinical data, medical history and the like. Based on the available information, the physician is able to adjust (or titrate) the device therapy 1672 and/or the medical therapy 1676.

Defining, Identifying and Using Predetermined Health-Related Events

Figure 17:
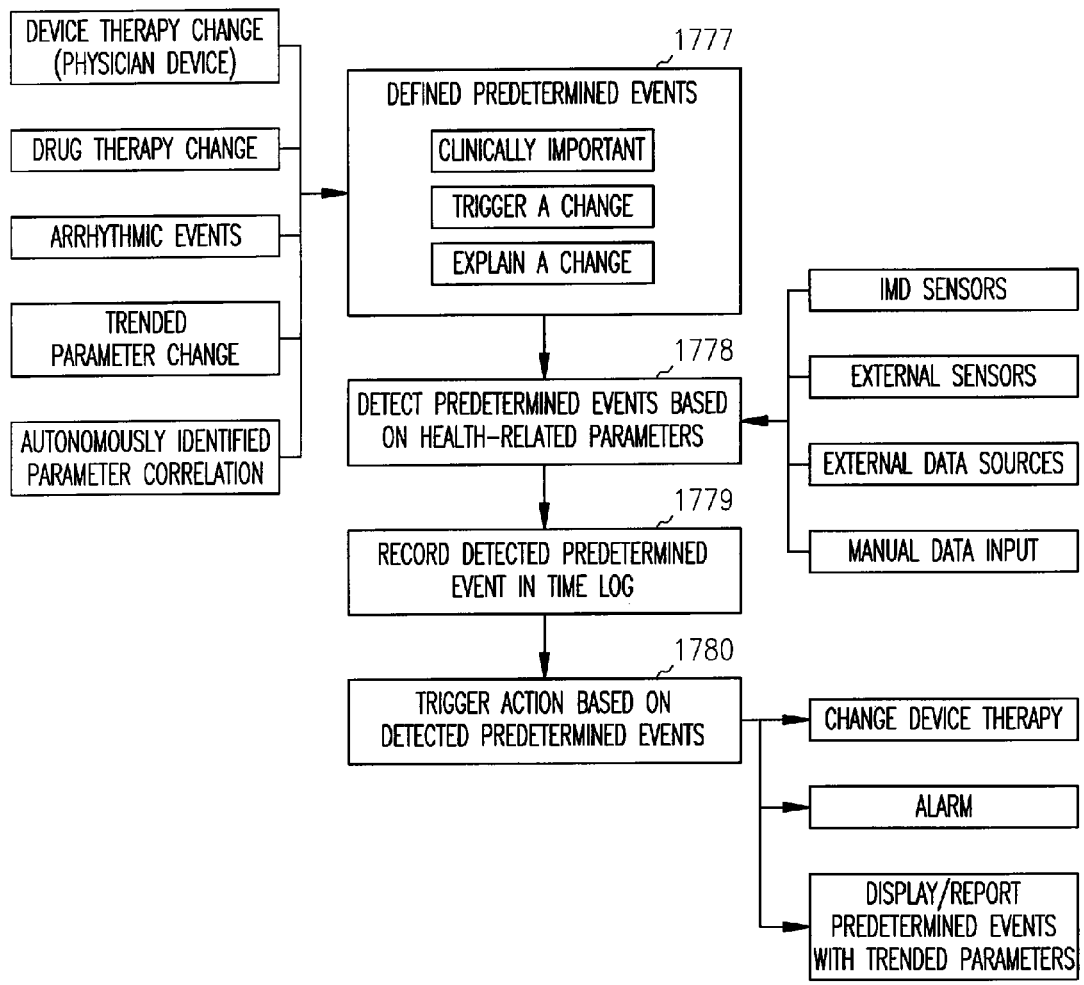
FIG. 17 illustrates a method for managing a patient's health by defining, detecting and using predetermined health-related events, according to various embodiments of the present subject matter.
Figure 18:
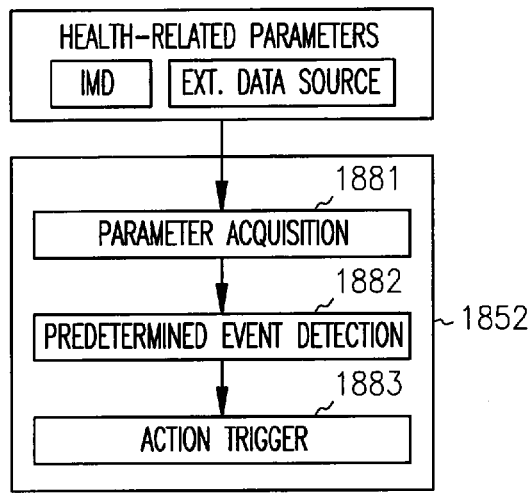
FIG. 18 illustrates a device (such as a WMD or IMD) for monitoring a patient's health condition that is capable of detecting predetermined health-related events, according to various embodiments of the present subject matter.
Figure 19:
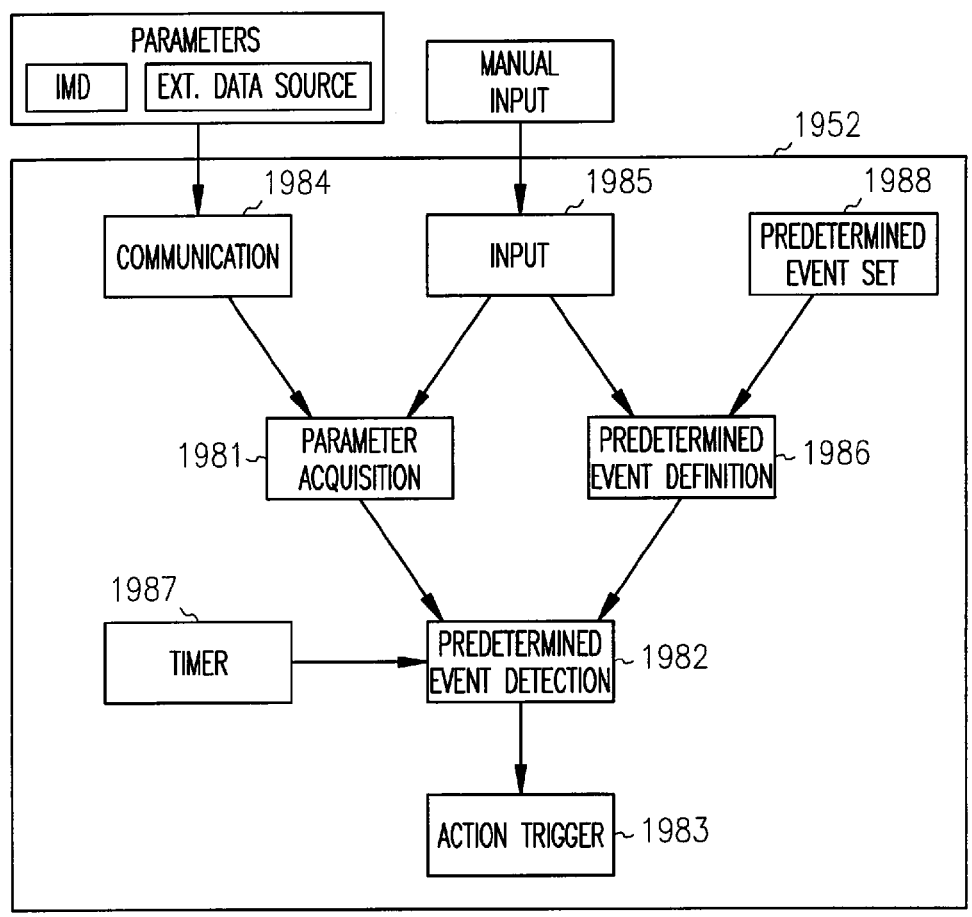
FIG. 19 illustrates a wellness monitoring device (WMD) for monitoring a patient's health condition that is capable of detecting predetermined health-related events, according to various embodiments of the present subject matter.

FIGS. 17-19 illustrate various embodiments of the present subject matter related to defining, identifying and using predetermined health-related events. In various embodiments, a device such as a WMD or IMD defines, identifies, displays and triggers actions based on a predetermined health-related event. In various embodiments, the predetermined events include significant events that are clinically important. Significant events includes those events that are clinically important in themselves (such as ventricular fibrillation), those events that trigger an important change (such as loss of ventricular pacing) or those events that explain a change (such as increased anxiety).

FIG. 17 illustrates a method for managing a patient's health by defining, detecting and using predetermined health-related events, according to various embodiments of the present subject matter. At 1777, predetermined events are defined. In various embodiments, predetermined events are significant health-related events, such as events that are clinically important in themselves, events that trigger a change, and/or events that explain a change. Examples of predetermined events includes device (e.g. IMD) therapy changes initiated by the device and/or clinician, a drug therapy change initiated by the device and/or clinician, arrhythmic events, changes in trended parameters, and autonomously-identified parameter correlations.

At 1778, predetermined health-related events are detected based on health-related parameters. In various embodiments, the health-related parameters are acquire through IMD sensors, external sensors, external data sources such as patient databases, and/or manual data inputs. At 1779, the detected event is recorded in a time log. In various embodiments, a time stamp is associated with the event to record the time of the event.

At 1780, an action is triggered based on the detected events. In various embodiments, the triggered action includes a change in device therapy, an alarm and/or a display or report of the predetermined events along with trended health-related parameters. In various embodiments, the triggered action includes initiating a signal for use within the device(s) that detected the events for transmission for use by other device(s).

FIG. 18 illustrates a device (such as a WMD or IMD) for monitoring a patient's health condition that is capable of detecting predetermined health-related events, according to various embodiments of the present subject matter. The illustrated device includes a parameter acquisition module 1881 to acquire health related parameters. These health-related parameters can include IMD parameters (whether sensed or device interrogated), and parameters from external data sources such as sensors and databases. Various embodiments acquire various health-related parameters that are provided throughout this disclosure. The illustrated device 1852 further includes a predetermined event detection module in communication with the parameter acquisition module. The predetermined event detection module 1882 communicates with the parameter acquisition module 1881 to determine whether the health-related parameter(s) correspond to at least one of the number of predetermined events. The illustrated device further includes an action trigger module 1883 to communicate with the predetermined event detection module and trigger at least one action appropriate for a detected predetermined event.

FIG. 19 illustrates a wellness monitoring device (WMD) for monitoring a patient's health condition that is capable of detecting predetermined health-related events, according to various embodiments of the present subject matter. The illustrated device 1952 includes a communication module 1984, a parameter acquisition module 1981, an input module 1985, a predetermined event definition module 1986, a timer module 1987 and a predetermined event detection module 1982. In operation, the modules perform the functions as described below.

The communication module 1984 receives at least one health-related parameter. The parameter acquisition module 1981 communicates with the communication module to acquire the at least one health-related parameter. The input module 1985 receives manual input data, such as data for defining predetermined events and/or parameters to be acquired by the parameter acquisition module 1981 through a communication link. The predetermined event definition module 1986 communicates with the input module 1985 and/or a memory storage that contains a set of predetermined health-related events 1988 to define a number of predetermined events for the patient's health condition. The predetermined event detection module 1982 communicates with the parameter acquisition module 1981 and the predetermined event definition module 1986 to determine that the health-related parameter(s) correspond to at least one of the number of predetermined events. The predetermined event detection module 1982 further communicates with the timer module 1987 to associate a time with the at least one of the number of predetermined events.

Various embodiments of the present subject matter include an action trigger module 1983 in communication with the predetermined event detection module. The action trigger module 1983 is adapted to trigger a desired action based on a detected predetermined event. In various embodiments, the action trigger is adapted to provide a signal to display the detected predetermined event along with a trend for the at least one health related parameter. In various embodiments, the device includes a display on which the predetermined event and the trend for the at least one health related parameter are displayed. In various embodiments, the signal is transmitted to another device with a display on which the predetermined event and the trend for the at least one health related parameter are displayed. In various embodiments, the action trigger is adapted to provide a signal to send an alarm in response to the detected predetermined event. Various embodiments of the present subject matter include an action trigger to provide a signal to change device therapy in response to the detected predetermined event.

The health-related parameters acquired by the parameter acquisition module 1981 are capable of including IMD parameters or health-related parameters from an external data source such as external sensors, patient history databases, databases accessible through a global computer network (e.g. Internet), and user inputs (e.g. manual inputs from a patient and/or clinician).

Reporting Multiple Health-Related Parameters

Figure 20:
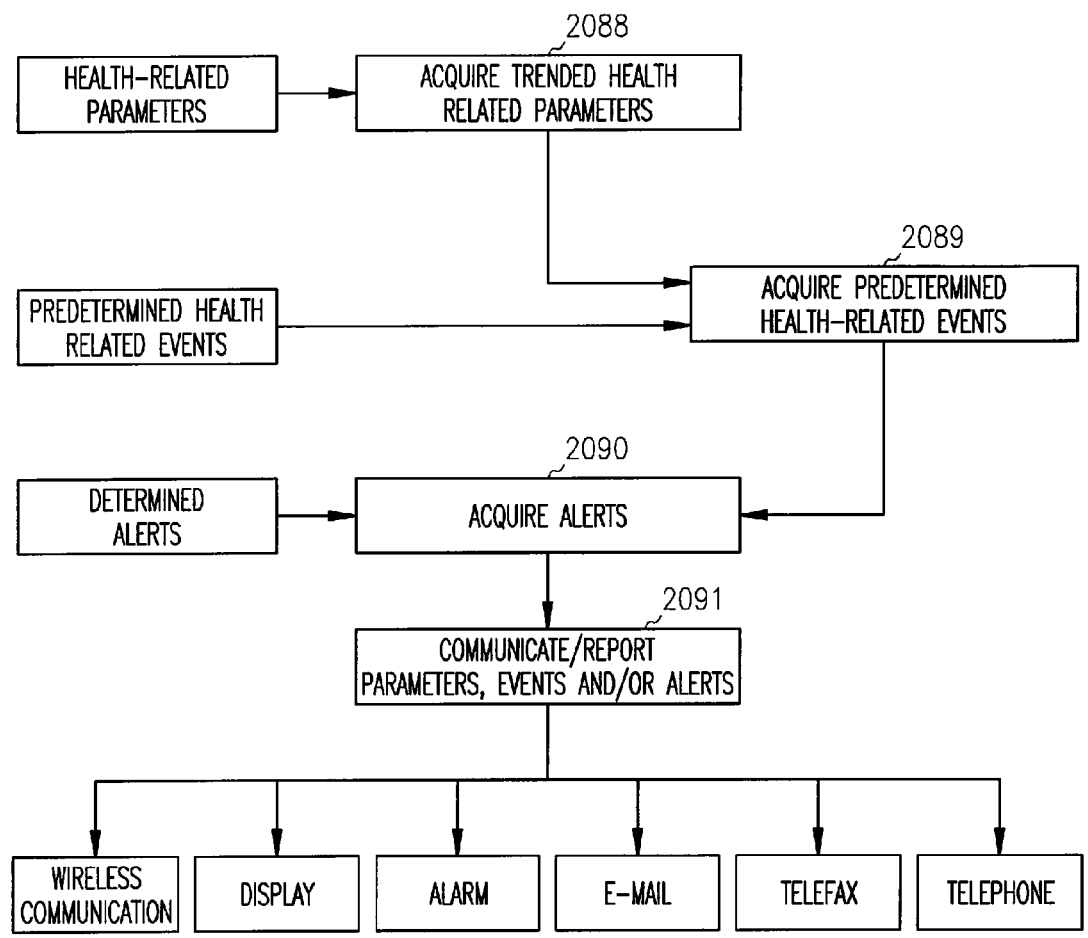
FIG. 20 illustrates a method for reporting multiple parameters related to a health condition of a patient, according to various embodiments of the present subject matter.
Figure 21:
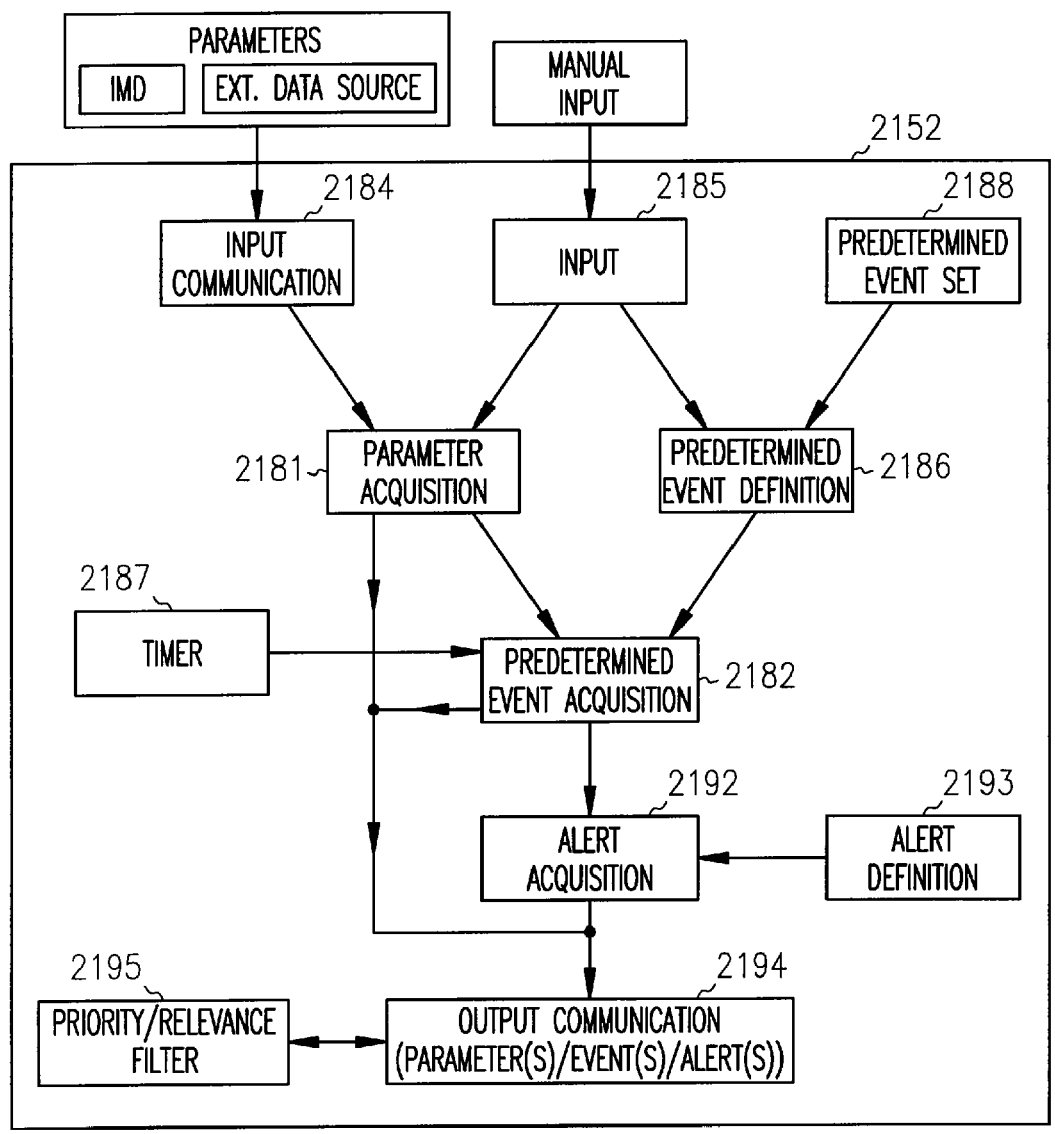
FIG. 21 illustrates a device (such as a WMD or IMD) for monitoring a patient's health condition that is capable of prioritizing communication of health-related parameters, according to various embodiments of the present subject matter.

FIGS. 20-21 illustrate various embodiments of the present subject matter related to reporting multiple health-related parameters. Various embodiments of the present subject matter provide a number of methods for transferring trended data, predetermined events and alerts to a clinician. In various embodiments, this type of information is capable of being displayed on a programmer screen or being otherwise used by a WMD and/or IMD within an advanced patient management system, such as those described within this disclosure, for example. This information is filtered in various embodiments of the present subject matter such that only the most relevant or clinically useful information is displayed or otherwise used.

FIG. 20 illustrates a method for reporting multiple parameters related to a health condition of a patient, according to various embodiments of the present subject matter. At 2088, a number of trended health-related parameters are acquired. In various embodiments, the trended health-related parameters include any of the various parameters described within this disclosure. In various embodiments, acquiring the trended health-related parameters includes acquiring parameters and trending the acquired parameters. At 2089, a number of predetermined events are acquired. In various embodiments, the predetermined events include events that are clinically important in themselves, events that trigger a change, or events that explain a change. In various embodiments, acquiring predetermined events include determining that the event is a significant health-related event as provided elsewhere in this disclosure. At 2090, a number of alerts are acquired. In various embodiments, acquiring alerts includes determining alerts. Alerts in various embodiments of the present subject matter include device-initiated alerts, patient-initiated alerts, and clinician-initiated alerts. Additionally, alerts in various embodiments of the present subject matter include alerts directed to the patient and alerts directed to a clinician.

At 2091, the present subject communicates at least one of the parameters, events and/or alerts. Various embodiments prioritize or characterize the relevance of the parameters, events and/or alerts, and appropriately communicate the information according to the relevance of the information. In various embodiments, the parameters, events and/or alerts are communicated in a report-like manner. Various embodiments of the present subject matter communicate the parameters, events and/or alerts incorporating a variety of communication technologies provided in this disclosure. In various embodiments, the communication displaying the parameters, events and/or alerts, providing an alarm signal with respect to the parameters, events and/or alerts, transmitting an e-mail, transmitting a telefax, placing a telephone call, and conducting wireless communication.

FIG. 21 illustrates a wellness monitoring device (WMD) for monitoring a patient's health condition that is capable of prioritizing communication of health-related parameters, according to various embodiments of the present subject matter. The illustrated device 2152 includes a communication module 2184, a parameter acquisition module 2181, an input module 2185, a predetermined event definition module 2186, a predetermined event set 2188, a timer module 2187, a predetermined event detection/acquisition module 2182, and an alert acquisition module 2192. In operation, the modules perform the following functions. The communication module 2184 receives at least one health-related parameter. The parameter acquisition module 2181 communicates with the communication module 2184 to acquire the at least one health-related parameter. The input module 2185 receives manual input data, such as data for defining predetermined events and/or parameters acquired by the parameter acquisition module 2181 through a communication link. The predetermined event definition module 2186 communicates with the input module 2185 to define a number of predetermined events for the patient's health condition. The predetermined event detection/acquisition module 2182 communicates with the parameter acquisition module 2181 and the predetermined event definition module 2186 to determine that the health-related parameter(s) correspond to at least one of the number of predetermined events. The predetermined event acquisition module 2182 further communicates with the timer module 2187 to associate a time with the at least one of the number of predetermined events. The alert acquisition module 2192 communicates with the predetermined event acquisition module 2182 and with an alert definition module 2193 to determine alerts from, among other things, the acquired predetermined events.

Various embodiments of the present subject matter include an output communication module 2194 in communication with the alert acquisition module 2192, the predetermined event acquisition module 2182 and the parameter acquisition module 2181. In various embodiments, the output communication module 2194 is in communication with a priority filter 2195 for characterizing or classifying the relevance of the parameter(s), event(s) and/or alert(s). The output communication module 2194 is adapted to appropriately communicate the parameter(s), event(s) and/or alert(s) using various communication technologies based on their relevance.

One of ordinary skill in the art will understand, upon reading and comprehending this disclosure, how to acquired parameters, events and/or alerts using an IMD, and transmitting a communication signal represented the acquired parameters, events and/or alerts from the IMD to assist with managing a patient's health.

Environmental Data

Figure 22:
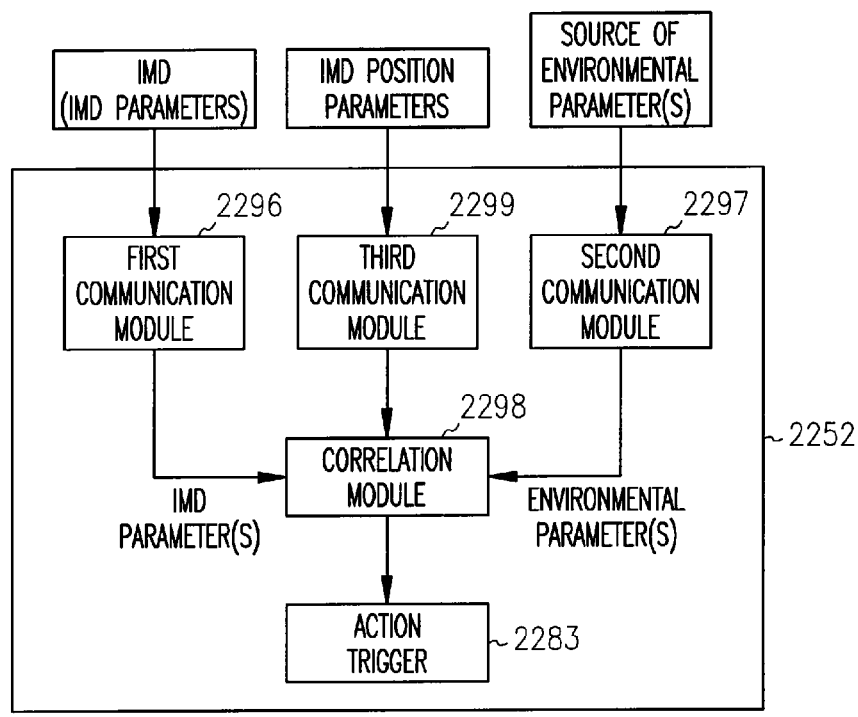
FIG. 22 illustrates a device (such as a WMD or IMD) for monitoring a patient's health condition that is capable of synthesizing environmental parameters with IMD parameters, according to various embodiments of the present subject matter.

FIG. 22 illustrates various embodiments of the present subject matter related to reporting environmental data. Various embodiments of the present subject matter automatically acquire and present environmental data to the attending physicians and/or patients for disease diagnosis and therapy decision making. For example, chronically ill patients can be very sensitive to the environment changes such as air quality and temperature. Patients who have respiratory disorders secondary to cardiovascular diseases (e.g. HF) may be vulnerable to certain environmental conditions. For example, acute exacerbation sometimes can be attributed to environmental changes. In various embodiments, a device (such as an IMD and/or WMD) is able to automatically acquire environmental data and provide such information in correlation to other measurements of the patient conditions to the clinician and/or patient.

FIG. 22 illustrates a device (such as a WMD or IMD) for monitoring a patient's health condition that is capable of synthesizing environmental parameters with implantable medical device (IMD) parameters, according to various embodiments of the present subject matter. Examples of environmental parameter types include, but are not limited to, parameters related to altitude, temperature, air quality, pollen count, and humidity. The illustrated device 2252 includes a first communication module 2296 for receiving IMD parameters, and a second communication module 2297 for receiving environmental parameters from a source of environmental parameters (such as an external sensor or a database). The device includes a correlation module 2298 that receives the IMD parameter(s) and the environmental parameter(s), and correlates the environmental parameters with the IMD parameters.

Various embodiments of the present subject matter include an action trigger module 2283 in communication with the correlation module 2298. The action trigger module 2283 is adapted to trigger a desired action based on the IMD parameter(s) and the environmental parameter(s). In various embodiments, the action trigger module 2283 is adapted to provide a signal to display the correlation between the IMD parameter(s) and the environmental parameter(s).

In various embodiments, the device 2252 includes a display on which the correlation between the IMD parameter(s) and the environmental parameter(s) is displayed. In various embodiments, the signal is transmitted to another device with a display on which the correlation between the IMD parameter(s) and the environmental parameter(s) is displayed. In various embodiments, the action trigger is adapted to provide a signal to send an alarm in response to the correlation between the IMD parameter(s) and the environmental parameter(s). Various embodiments of the present subject matter include an action trigger module 2283 to provide a signal to change device therapy in response to the correlation between the IMD parameter(s) and the environmental parameter(s).

In various embodiments, the device 2252 further includes a third communication module 2299 to receive IMD position parameters. Thus, for example, in an embodiment in which the second communication module is accessing environmental parameter(s) from a database of regional environmental parameters, the present subject matter is capable of determining the appropriate region for which to retrieve environmental parameters. Additionally, in various embodiments, the IMD position parameters include parameters indicative of altitude. According to various embodiments, the IMD position parameters are generated using cellular technology to determine a cell region, GPS technology, and manual data inputs.

Various embodiments of the present subject matter relate to an advanced patient management system. In various embodiments, the system includes at least one implantable medical device (IMD) to acquire at least one IMD parameter indicative of patient wellness, means to acquire at least one environmental parameter from at least one external source, and means to factor in the at least one environmental parameter in the advanced patient management system. In various embodiments, the environmental parameter is factored in by adjusting the IMD parameter based on the at least one environmental parameter. In various embodiments, the environmental parameter is factored in by adjusting a display of the IMD parameter. In various embodiments, the environmental parameter is factored in by adjusting IMD-provided therapy (such as electrical therapy, drug therapy, and the like). A number of environmental parameter types are acquired in various embodiments. Examples of these environmental types include altitude, temperature, air quality, pollen counts, humidity, and pressure. In various embodiments, the IMD parameter(s) and/or the environmental parameter(s) are trended and/or correlated, as provided in this disclosure.

Identifying, Displaying and Assisting in Correlating Health-Related Data

Figure 23:
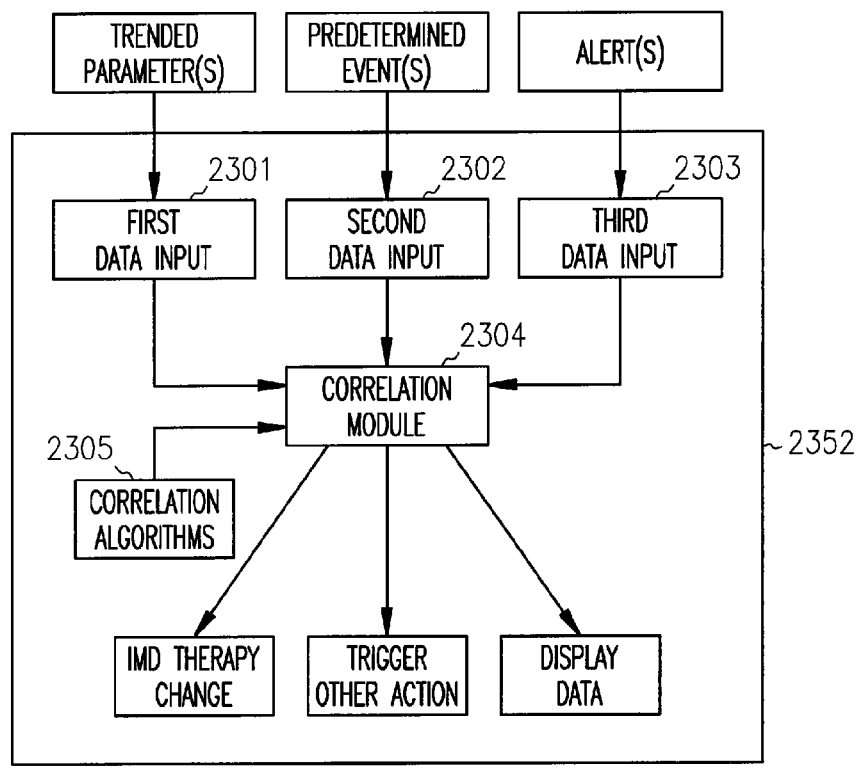
FIG. 23 illustrates a device (such as a WMD or IMD) for monitoring a patient's health condition that is capable of correlating trended parameters, predetermined events, and alerts, according to various embodiments of the present subject matter.

FIG. 23 illustrates various embodiments of the present subject matter related to identifying, displaying and assisting in data correlation. One definition of correlation is a relation existing between phenomena or things or between mathematical or statistical variables which tend to vary, be associated, or occur together in a way not expected on the basis of chance alone. Correlating data involves showing a reciprocal, mutual, and/or causal relationship among the data.

Various embodiments of the present subject matter provide methods of correlating, or assisting in the correlation of, trended data, predetermined events and other actions taken by the system (such as an alert transmitted to the clinician). Various embodiments of the present subject matter autonomously identify correlations and display the identified correlations. For example, various embodiments determine correlations without human intervention. In various embodiments, the present subject matter assists the clinician in correlating the information by displaying the data in an appropriate manner. Cause and effect relationships that are suitable for use in treating patients can be established by correlating data items.

FIG. 23 illustrates a device (such as a WMD or IMD) for monitoring a patient's health condition that is capable of correlating trended parameters, predetermined events, and alerts, according to various embodiments of the present subject matter. The illustrated device 2352 includes a first data input 2301 to receive trended health-related parameter(s), a second data input 2302 to receive predetermined event(s) associated with a patient's health, and a third data input 2303 to receive alert(s) associated with a patient's health. According to various embodiments of the present subject matter, the health-related parameters, the predetermined events, and the alerts include any of the health-related parameters, the predetermined events, and the alerts provided throughout this disclosure.

The device 2352 includes a correlation module 2304 in communication with the first data input 2301, the second data input 2302, and the third data input 2303. The correlation module 2304, which in uses various correlation algorithms 2305 in various embodiments, is adapted to correlate at least one of one or more trended health-related parameters, one or more health-related predetermined events, and one or more health-related alerts. In various embodiments, the correlation module 2304 is adapted to trigger an action. In various embodiments, the action is automatically triggered based on the correlation. In various embodiments, the correlation module automatically triggers an IMD therapy change based on the correlation. In various embodiments, the correlation module automatically displays the correlation. For example, a cursor or other indicator can be used to highlight the correlation.

Those versed in the art will understand, upon reading and comprehending this disclosure, how to incorporate various well known techniques for computing correlations between two or more data sources. For example, in the case of providing correlations between two data sources, Pearson's product-moment correlations is one example of a type of correlation that may be computed. In the case of three or more data sources, multivariate correlation techniques may be employed.

According to various embodiments of the present subject matter, the choice of which data sources to correlate is based on knowledge of physiological coupling between the sources. According to various embodiments, the choice of which data sets to correlate and the time durations(s) over which the correlations are computed is determined at the start of monitoring, and is either the same for each patient, or is tailored to individual patients based on the physicians' knowledge of the patient's condition. In various embodiments, the decisions of which parameters to correlate with each other may be dynamically selected based on ongoing IMD or WMD monitoring of the patient's physiology.

Composite Parameter Indices

Figure 24:
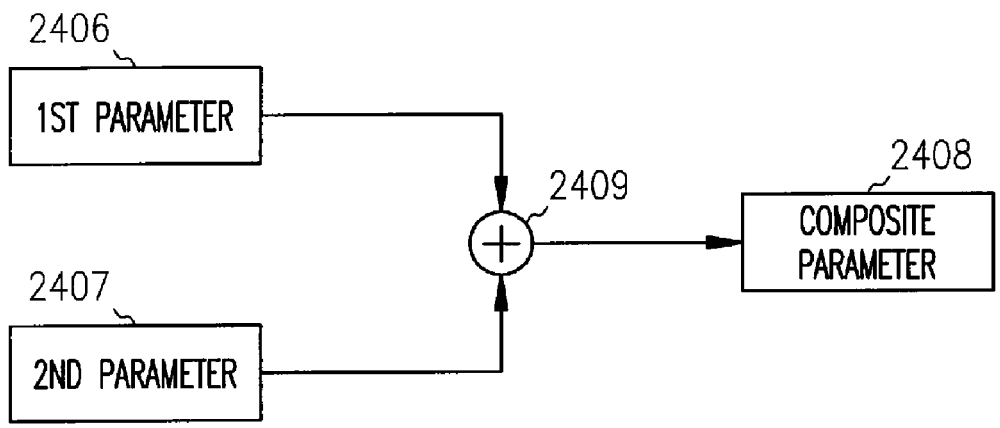
FIG. 24 illustrates a method to generate composite parameters for use in managing a patient's health, according to various embodiments of the present subject matter.
Figure 25:
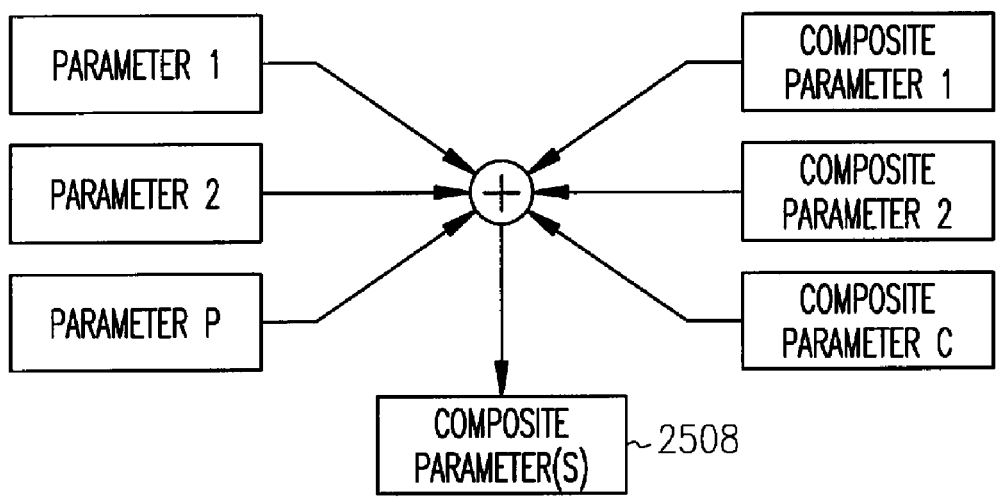
FIG. 25 illustrates a method to generate composite parameters for use in managing a patient's health, according to various embodiments of the present subject matter.
Figure 26:
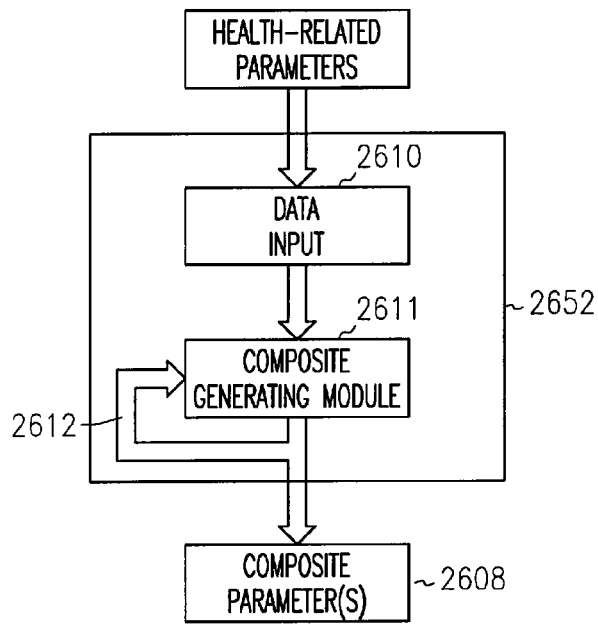
FIG. 26 illustrates a device (such as a WMD or IMD) for monitoring a patient's health condition that is capable of generating composite parameters, according to various embodiments of the present invention.

FIGS. 24-26 illustrate various embodiments of the present subject matter related to defining, identifying and utilizing composite parameter indices. A composite parameter is a parameter created by combining two or more parameter inputs. For example an exercise conditioning composite parameter is generated by dividing a heart rate by an activity level. A lower exercise condition composite parameter indicates that a patient is in better condition. Various embodiments of the present subject matter provide composite parameters that function as trended parameters in various manner in which the trended parameters are used, as provided throughout this disclosure. A composite parameter is capable of being used in any way a raw parameter is used, such as displaying, correlating, defining predetermined events, defining alerts, and the like.

FIG. 24 illustrates a method to generate composite parameters for use in managing a patient's health, according to various embodiments of the present subject matter. The method illustrates a first parameter 2406 and a second parameter 2407 being operated on to form a composite parameter 2408. One or ordinary skill in the art will understand, upon reading and comprehending this disclosure, that the operation denoted at 2409 can be any number of mathematical and/or logical operations. For example, the composite parameter 2408 can be formed by multiplying the first parameter 2406 and the second parameter 2407, or can be formed by dividing the second parameter 2407 into the first parameter 2406. More complex mathematical and/or logical operations can be used to generate the composite index.

FIG. 25 illustrates a method to generate composite parameters for use in managing a patient's health, according to various embodiments of the present subject matter. The method illustrates a number of parameters (1, 2, P) and a number of composite parameters (1, 2, C) that are capable of being combined to form one or more composite parameters 2508. Thus, the present subject matter is capable of generating a composite parameter from any number of health-related parameters, from any number of previously-determined composite parameters, or from any combination of one or more parameters and one or more composite parameters.

In various embodiments, the parameters include IMD-measured parameters and/or IMD-interrogated parameters. IMD-interrogated parameters include, for example, parameters related to a device status such as battery or lead impedance. In various embodiments, the parameters include user-inputted parameters provided by a patient, clinician or other person.

Various embodiments of the present subject matter combine two or more health-related parameters related to a body system to generate a composite parameter that is indicative of the health of the body system. For example, respiratory rate, tidal volume, maximum oxygen consumption (VO2) and periodic breathing parameters relate to a respiratory system. These parameters can be used to generate a single composite parameter index that provides a health indication concerning the respiratory system. Another example uses an average heart rate and an activity parameter to generate a composite parameter index indicative of physical conditioning. Other examples use cardiac output and vascular pressures to measure vascular resistance. Another example measures respiration and heart rate to measure respiratory sinus arrhythmia.

In various embodiments, the composite index is displayed with trended health-related parameter(s), predetermined event(s) and/or alert(s). In various embodiments, the composite parameter is used to define a predetermined health-related event. In various embodiments, the composite parameter is used to define a clinician alert. In various embodiments, the composite parameter is used to modify device therapy.

FIG. 26 illustrates a device (such as a WMD or IMD) for monitoring a patient's health condition that is capable of generating composite parameters, according to various embodiments of the present invention. The illustrated device 2652 includes a data input 2610 to receive two or more health-related parameters and a composite generating module 2611 in communication with the data input 2610. In operation, the composite generating module 2611 receives the health-related parameters and generates a composite parameter 2608 using the health-related parameters. The composite generating module 2611 is capable of performing any number of mathematical and/or logical operations, such as that denoted at 2409 in FIG. 24. In various embodiments, the composite generating module 2611 is capable of combining one or more composite parameters (represented by line 2612) with one or more health-related parameters to form other composite parameters.

Various embodiments provide various composite parameters. A number of these composite parameters are identified below. The identified composite parameters is not intended to be an exclusive list of the available composite parameters.

In a first example, a composite parameter indicative of systemic vascular resistance (SVR) is generated using an acquired cardiac output parameter (C.O.), a mean arterial pressure parameter ($/P_{ART}$), and a mean right atrial pressure parameter ($/P_{RA}$). In various embodiments, the SVR composite parameter is provided by:

$$SVR = \frac{\overline{P_{ART}} - \overline{P_{RA}}}{C.O.}.$$

In a second example, a composite parameter indicative of pulmonary vascular resistance (PVR) is generated using an acquired cardiac output parameter (C.O.), a mean pulmonary artery pressure parameter ($/P_{PA}$), and one of a mean pulmonary capillary wedge pressure parameter ($/P_{CW}$) and a mean left atrial pressure parameter ($/P_{LA}$). In various embodiments, the PVR composite parameter is provided by:

$$PVR = \frac{\overline{P_{PA}} - \overline{P_{CW}}}{C.O.}, \text{ or}$$

$$PVR = \frac{\overline{P_{PA}} - \overline{P_{LA}}}{C.O.}.$$

In a third example, a composite parameter indicative of respiratory sinus arrhythmia (RSA) is generated using an acquired heart rate parameter ($P_{HR}$) and a parameter related to instantaneous lung volume ($P_{LV}$). For example, a trans-thoracic sensor can be used in the acquisition. In various embodiments, the RSA composite parameter is provided by:

$RSA = f(P_{HR}, P_{LV}).$

In a fourth example, a composite parameter indicative of a degree of dyspnea (D) is generated using an acquired respiration rate parameter ($P_{RR}$) and a tidal volume parameter ($P_{TV}$). In various embodiments, the dyspnea composite parameter is provided by:

$$D = \frac{P_{RR}}{P_{TV}}.$$

Context may temporarily affect the physiological condition of a monitored patient. A patient context (or body-related concept), for example, may include posture, activity level, mental/emotional state and the like. Examples of patient contexts include sleeping or lying down, running, and driving. An environmental context (or external factor), for example, may include ambient temperature, sound level and the like. The concept of context has previously been discussed with respect to FIG. 16.

In various embodiments, the context is correlated with the physiologic measurements. In various embodiments, measurements are taken only for certain contexts so as to provide a repeatable baseline. For example, it is preferred to measure some parameters when a patient is at rest or in a known position. Thus, repeatable composite parameters can be generated. This is useful to determine trends or deviations from normal values. Additionally, various embodiments determine the context to provide an appropriate therapy for a contextual situation.

The following commonly-assigned patent applications refer to the use of multiple parameters and are herein incorporated by reference in their entirety: "Implantable Cardiac Rhythm Management Device For Assessing Status of CHF Patients," Ser. No. 09/434,009, filed Nov. 4, 1999, now U.S. Pat. No. 6,275,727; "Method and Apparatus For Determining Changes In Heart Failure Status,"Ser. No. 10/001,223, filed Nov. 15, 2001; and "Cardiac Rhythm Management Systems and Methods Predicting Congestive Heart Failure Status," Ser. No. 10/213,268, filed Aug. 6, 2002. The following commonly-assigned patent application refers to context and is herein incorporated by reference in its entirety: "Methods and Devices For Detection of Context When Addressing A Medical Condition of a Patient", Ser. No. 10/269,611, filed Oct. 11, 2002.

Triaging Health-Related Data

Figure 27:
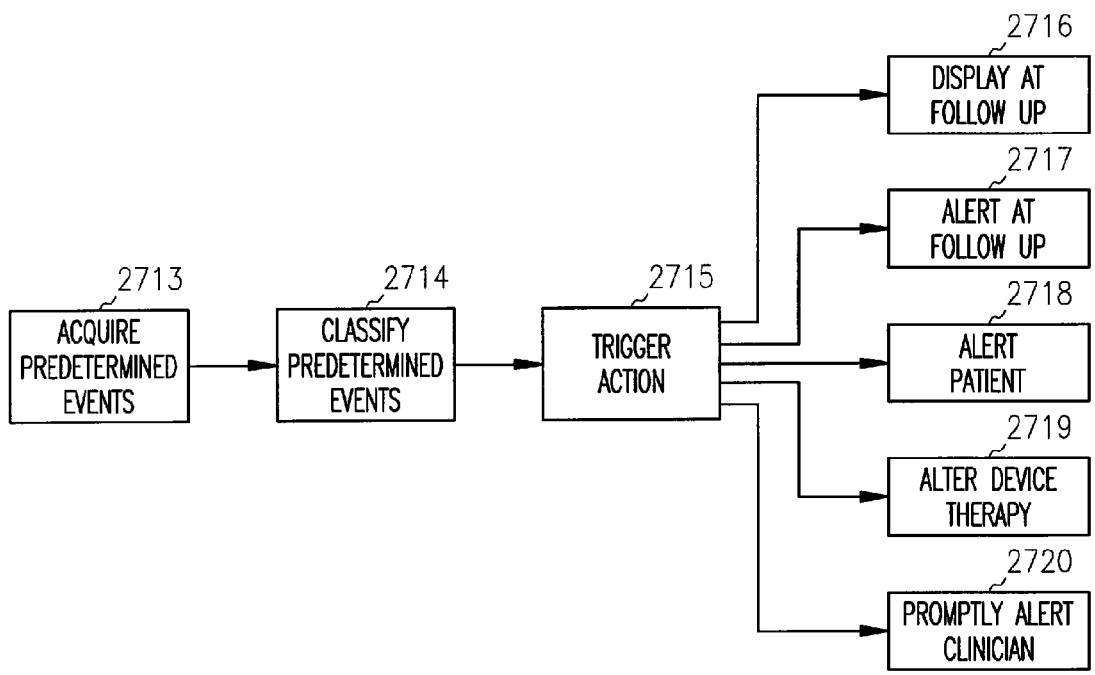
FIG. 27 illustrates a method to triage predetermined events for use in managing a patient's health, according to various embodiments of the present subject matter.
Figure 28:
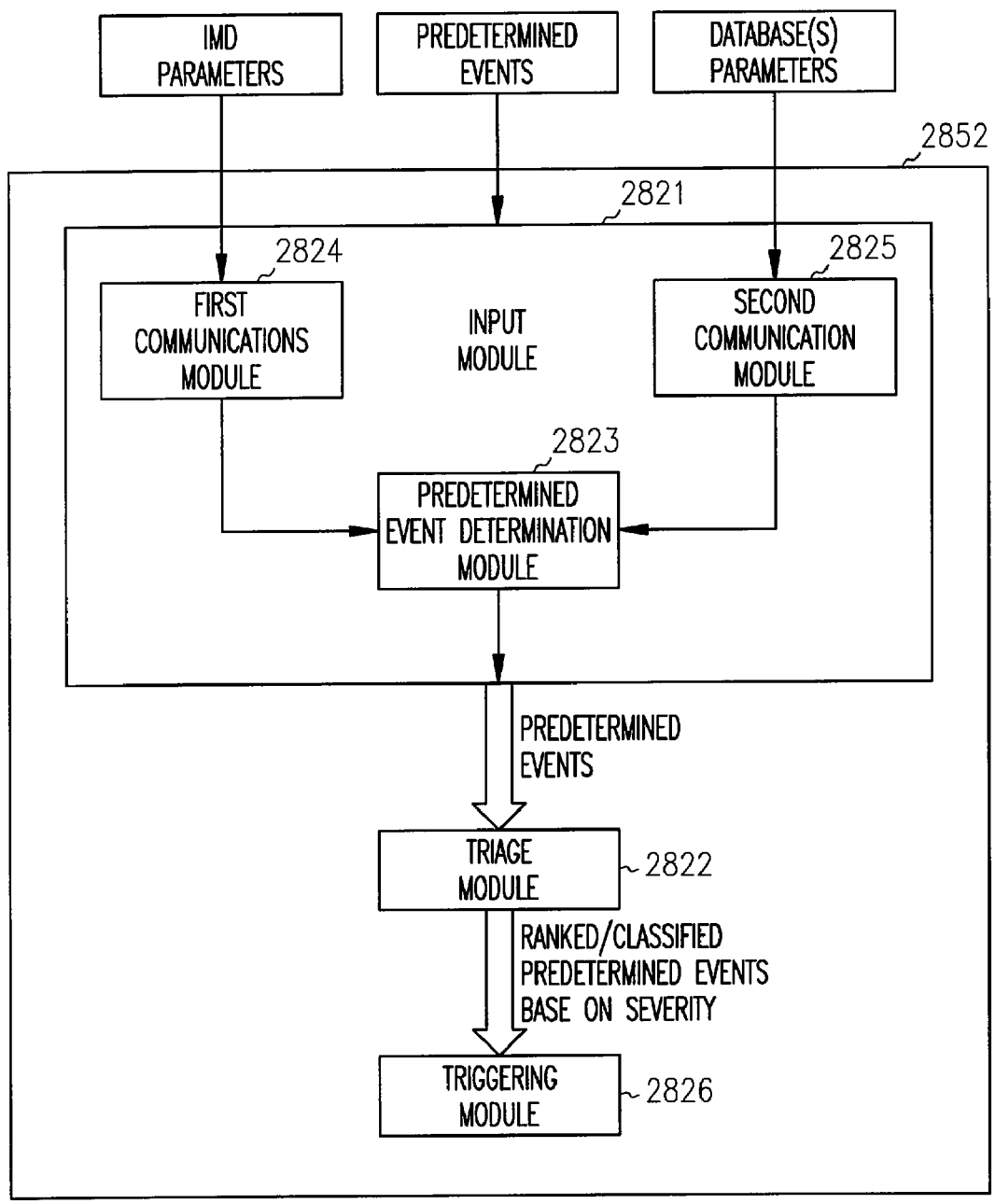
FIG. 28 illustrates a device (such as a WMD or IMD) for monitoring a patient's health condition that is capable of classifying a number of predetermined events according to severity, and performing a system action based on the classification, according to various embodiments of the present subject matter.

FIGS. 27-28 illustrates various embodiments of the present subject matter related to triaging health-related data in an advanced patient management system. Various embodiments of the present subject matter provide one or more devices (such as IMD, WMD, programmer and the like) with the ability to rank the severity of predetermined events. This ranking is used to prioritize the processing of the predetermined events and respond in an appropriate manner. For example, the system can be designed such that a modest increase in heart rate holds a lower priority and is related to the clinician at a next patient followup; whereas a sudden increases in weight (which may be associated with acute decompensation in a heart failure patient) may be assigned a higher priority and immediately be communicated to the clinician through various communication means.

FIG. 27 illustrates a method to triage predetermined events for use in managing a patient's health, according to various embodiments of the present subject matter. At 2713, predetermined events are acquired. At 2714, the acquired predetermined events are classified, ranked, sorted or filtered according to severity. At 2715, an action is triggered based on the severity of the predetermined event. According to various embodiments, the action includes one or more of displaying the predetermined event to a clinician at a patient followup visit 2716, alerting a clinician of the predetermined event at a patient followup visit 2717, initiating an alert for the patient 2718, altering device therapy 2719, and initiating an alert (such as a prompt emergency alert) to the clinician using an advance patient management system 2720. In various embodiments, the above-identified actions are performed for predetermined events that have been classified for increasing severity such that action 2716 is performed for a less severe event than action 2717, which is performed for a less severe event than action 2718, which is performed for a less severe event than action 2719, which is performed for a less severe event than action 2710. Other actions can be performed according to the severity of the predetermined event.

In various embodiments, the available actions to be performed are associated with various severity levels for predetermined events. This information is stored in a computer-readable memory such that a device is capable of performing an action that is associated with a detected predetermined event.

FIG. 28 illustrates a device (such as a WMD or IMD) for monitoring a patient's health condition that is capable of classifying a number of predetermined events according to severity, and performing a system action based on the classification, according to various embodiments of the present subject matter. The illustrated device 2852 includes an input module 2821 and a triage module 2822.

In various embodiments, the input module 2821 acquires predetermined events. In various embodiments, the input module 2821 includes a predetermined event determination module 2823 to determine whether a predetermined event has occurred. In various embodiments, the input module 2821 includes a first communication module 2824 to acquire IMD parameters for use by the predetermined event determination module 2823. In various embodiments, the input module 2821 includes a second communication module 2825 to acquire database parameters for use by the predetermined event determination module.

The triage module 2822 receives the predetermined event (s) and ranks or otherwise classifies, the predetermined events according to severity. In various embodiments, the device 2852 includes a triggering module 2826 in communication with the triage module 2822. The triage module 2822 is adapted to automatically initiate a desired action by the triggering module 2826 based on the severity of the predetermined event. In various embodiments, the action initiated is appropriate for the severity of the event. In various embodiments, a communication or report is initiated by the device when a predetermined event is classified as being more severe. For example, the communication can be an alarm or a prominently displayed message. In various embodiments, a communication or report is provided during a subsequent patient follow-up session when a predetermined event is classified as being less severe. In various embodiments, the device 2852 automatically performs a desired system action selected from a number of available system actions. The action is selected based on the severity of the predetermined event.

Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations of the present subject matter. It is to be understood that the above description is intended to be illustrative, and not restrictive. Combinations of the above embodiments, and other embodiments will be apparent to those of skill in the art upon reviewing the above description. The scope of the present subject matter should be determined with reference to the appended claims, along with the full scope of equivalents to which such claims are entitled.

What is claimed is:

1. A programmable device within an advanced patient management system, the device comprising a computer-readable medium with machine executable instructions stored thereon for performing a computer-executable process to report multiple parameters related to a health condition of a patient, the computer-executable process comprising:
   acquiring one or more trended health-related parameters;
   acquiring one or more predetermined events corresponding to the one or more trended health-related parameters, wherein each of the one or more predetermined events represents an event condition where a predetermined event definition is satisfied;
   acquiring one or more alerts associated with the one or more predetermined events, wherein each of the one or more alerts represents an alert condition where a predetermined alert definition is satisfied, and is distinct from each of the one or more events; and
   communicating the one or more trended health-related parameters, the one or more predetermined events, and the one or more alerts in a manner suitable for use in determining the health condition of the patient.

2. The device of claim 1, wherein communicating the one or more trended health-related parameters, the one or more predetermined events, and the one or more alerts includes displaying the one or more trended health-related parameters, the one or more predetermined events, and the one or more alerts in a single display area.

3. The device of claim 1, wherein the device includes a programmable implantable medical device (IMD) adapted to acquire the at least one health related parameter and adapted to communicate with a programmer adapted to display the one or more trended health-related parameters, the one or more predetermined events, and the one or more alerts.

4. The device of claim 1, wherein the device includes a wellness management device (WMD) adapted to display the one or more trended health-related parameters, the one or more predetermined events, and the one or more alerts.

5. The device of claim 4, wherein the one or more trended health-related parameters, the one or more predetermined events, and the one or more alerts to the number are displayed by the WMD in a manner suitable for viewing by a clinician.

6. The device of claim 4, wherein the one or more trended health-related parameters, the one or more predetermined events, and the one or more alerts to the number are displayed by the WMD in a manner suitable for viewing by a patient.

7. The device of claim 4, wherein the WMD includes a personal data assistant (PDA).

8. The device of claim 4, wherein the WMD includes a bedside monitor.

9. The device of claim 4, wherein the WMD includes a laptop computer.

10. The device of claim 4, wherein the WMD includes a desktop computer.

11. The device of claim 1, wherein the computer-executable process further comprises filtering the one or more trended health-related parameters, the one or more predetermined events, and the one or more alerts according to relevance to identify a relevant one or more trended health-related parameters, a relevant one or more predetermined events, and a relevant one or more alerts, and comprises displaying the relevant one or more trended health-related parameters, the relevant one or more predetermined events, and the relevant one or more alerts in a single display area.

12. The device of claim 1, wherein the one or more alerts indicate important changes with respect to the health of the patient.

13. The device of claim 1, wherein the one or more alerts indicate important negative changes with respect to the health of the patient.

14. The device of claim 1, wherein communicating the one or more trended health-related parameters, the one or more predetermined events, and the one or more alerts in a manner suitable for use in determining the health condition of the patient includes at least one of automatically displaying a report, automatically triggering an alarm, automatically sending an e-mail, automatically sending a telefax, and automatically placing a telephone call.

15. An advanced patient management system, including a programmable device comprising a computer-readable medium with machine executable instructions stored thereon for performing a computer-executable process to report multiple parameters related to a health condition of a patient, the computer-executable process comprising:
    defining predetermined events for the health of the patient, wherein each of the predetermined events represents an event condition where a predetermined event definition is satisfied;
    defining predetermined alerts for the health of the patient, wherein each of the predetermined alerts represents an alert condition where a predetermined alert definition is satisfied, and is distinct from each of the one or more events;
    acquiring health-related parameters;
    trending the health-related parameters;
    detecting at least one of the defined predetermined events based on the trended health-related parameters;
    associating the detected predetermined event with an alert; and
    communicating the trended health-related parameters, the detected predetermined event, and the alert in a manner suitable for use in determining the health condition of the patient.

16. The system of claim 15, wherein defining predetermined events includes defining a device therapy change that can affect a trended parameter.

17. The system of claim 15, wherein defining predetermined events includes defining a drug therapy change.

18. The system of claim 15, wherein defining predetermined events includes defining an arrhythmic event.

19. The system of claim 15, wherein defining predetermined events includes defining a clinically important change in the at least one trended parameter.

20. The system of claim 15, wherein defining predetermined events includes defining an autonomously identified correlation between two or more trended parameters as predetermined.

21. The system of claim 15 wherein the computer-executable process further comprises acquiring the acquired health-related parameters using at least one implantable medical device (IMD) sensor.

22. The system of claim 15, wherein the computer-executable process further comprises acquiring the acquired health-related parameters using at least one external sensor.

23. The system of claim 15, wherein the computer-executable process further comprises acquiring the acquired health-related parameters using at least one external data source.

24. The system of claim 15, wherein the computer-executable process further comprises acquiring the acquired health-related parameters using at least one manual data input.

25. The system of claim 15, wherein communicating the trended health-related parameters, the detected predetermined event, and the alert includes displaying the trended health-related parameters, the detected predetermined event, and the alert to a healthcare provider using a remote wellness monitoring device (WMD).

26. The system of claim 15, wherein communicating the trended health-related parameters, the detected predetermined event, and the alert includes displaying the trended health-related parameters, the detected predetermined event, and the alert to a healthcare provider using a programmer.

27. The system of claim 15, wherein communicating the trended health-related parameters, the at least one detected predetermined event, and the alert includes displaying the trended health-related parameters, the detected predetermined event, and the alert to the patient using a wellness monitoring device (WMD).

28. The system of claim 27, wherein the WMD includes a bedside monitor.

29. The system of claim 15, wherein the detected predetermined event includes events reflecting both positive changes and negative changes.

30. The system of claim 15, wherein communicating the trended health-related parameters, the detected predetermined event, and the alert includes displaying the detected predetermined event with the trended health-related parameters in a single display area.

31. The system of claim 15, wherein communicating the trended health-related parameters, the detected predetermined event, and the alert includes prominently displaying the alert on a programmer screen display.

32. The system of claim 31, wherein prominently displaying the alert on a programmer screen display includes displaying the alert on a sign-on screen of the programmer.

33. A device for reporting multiple parameters related to a health condition of a patient, comprising:
    a parameter acquisition module adapted to acquire at least one trended health-related parameter;
    a predetermined event acquisition module adapted to acquire at least one predetermined event corresponding to the at least one trended health-related parameter, wherein each of the at least one predetermined event represents an event condition where a predetermined event definition is satisfied;
    an alert acquisition module adapted to acquire at least one alert associated with the at least one predetermined event, wherein each of the at least one alert represents an alert condition where a predetermined alert definition is satisfied, and is distinct from each of the at least one event; and
    an output communication module adapted to communicate the at least one trended health-related parameter, the at least one predetermined event, and the the at least one alert in a manner suitable for use in determining the health condition of the patient.

34. The device of claim 33, wherein the at least one trended health-related parameter includes an environmental parameter, a diet parameter or a mental/emotional parameter.

35. The device of claim 33, further comprising a filter module adapted to communicate with the output communication module and to prioritize the at least one trended health-related parameter, the at least one predetermined event, and the at least one event according to relevance such that the output communication module communicates higher priority parameters, events and alerts in a preferred manner over lower priority parameters, events and alerts.

36. An advanced patient management system for reporting multiple parameters related to a health condition of a patient, comprising:

means for acquiring at least one trended health-related parameter, at least one predetermined event corresponding to the at least one trended health-related parameter, and at least one alert associated with the at least one predetermined event, wherein each of the at least one predetermined event represents an event condition where a predetermined event definition is satisfied, and each of the at least one alert represents an alert condition where a predetermined alert definition is satisfied, and is distinct from each of the at least one event; and means for communicating the at least one trended health-related parameter, the at least one predetermined event, and the at least one alert in a manner suitable for use in determining the health condition of the patient.

37. The system of claim 36, wherein the at least one trended health-related parameter includes an environmental parameter, a diet parameter or a mental/emotional parameter.

38. The system of claim 36, further comprising means for prioritizing the at least one trended health-related parameter, the at least one predetermined event, and the at least one alert according to relevance such that higher priority parameters, events and alerts are preferably communicated over lower priority parameters, events and alerts.

* * * * *

UNITED STATES PATENT AND TRADEMARK OFFICE
CERTIFICATE OF CORRECTION

| | | |
|---|---|---|
| PATENT NO. | : 7,983,759 B2 | Page 1 of 1 |
| APPLICATION NO. | : 10/323606 | |
| DATED | : July 19, 2011 | |
| INVENTOR(S) | : Jeffrey E. Stahmann et al. | |

It is certified that error appears in the above-identified patent and that said Letters Patent is hereby corrected as shown below:

In column 32, line 51, in Claim 33, after "the" delete "the".

Signed and Sealed this
Twenty-seventh Day of December, 2011

David J. Kappos
*Director of the United States Patent and Trademark Office*